(12) United States Patent
Gifford, III et al.

(10) Patent No.: US 12,232,955 B2
(45) Date of Patent: Feb. 25, 2025

(54) MODULAR VALVE REPLACEMENT SYSTEMS AND ASSOCIATED DEVICES AND METHODS OF USE

(71) Applicant: THE FOUNDRY, Menlo Park, CA (US)

(72) Inventors: Hanson S. Gifford, III, Menlo Park, CA (US); James I. Fann, Menlo Park, CA (US); Matthew McClean, Menlo Park, CA (US); Gaurav Krishnamurthy, Menlo Park, CA (US); Vrad Levering, Menlo Park, CA (US); Neil Zimmerman, Menlo Park, CA (US)

(73) Assignee: The Foundry, Menlo Park, CA (US)

( * ) Notice: Subject to any disclaimer, the term of this patent is extended or adjusted under 35 U.S.C. 154(b) by 929 days.

(21) Appl. No.: 17/282,994

(22) PCT Filed: Oct. 7, 2019

(86) PCT No.: PCT/US2019/055063
§ 371 (c)(1),
(2) Date: Apr. 5, 2021

(87) PCT Pub. No.: WO2020/073056
PCT Pub. Date: Apr. 9, 2020

(65) Prior Publication Data
US 2021/0338419 A1 Nov. 4, 2021

Related U.S. Application Data

(60) Provisional application No. 62/851,595, filed on May 22, 2019, provisional application No. 62/766,193, (Continued)

(51) Int. Cl.
*A61F 2/24* (2006.01)

(52) U.S. Cl.
CPC .... *A61F 2/2409* (2013.01); *A61F 2220/0008* (2013.01); *A61F 2230/0034* (2013.01);
(Continued)

(58) Field of Classification Search
CPC ............ A61F 2/2409; A61F 2220/0008; A61F 2230/0034; A61F 2250/001;
(Continued)

(56) References Cited

U.S. PATENT DOCUMENTS

2008/0208332 A1 * 8/2008 Lamphere ............. A61F 2/2436
623/2.38
2009/0088836 A1 4/2009 Bishop et al.
(Continued)

FOREIGN PATENT DOCUMENTS

WO 2010077676 A1 7/2010
WO 2012054776 A1 4/2012
(Continued)

OTHER PUBLICATIONS

Extended European Search Report mailed Jul. 11, 2022 in International Patent Application No. PCT/US2019/055063, 8 pages.
(Continued)

*Primary Examiner* — Sarah W Aleman
*Assistant Examiner* — Rachel S Highland
(74) *Attorney, Agent, or Firm* — Perkins Coie LLP

(57) ABSTRACT

The present technology relates to modular valve replacement systems for treating valve-related cardiac disorders. In select embodiments, the modular valve replacement system includes a fixation device and a permanent valve assembly. The fixation device and the permanent valve assembly are delivered separately, enabling use of smaller delivery systems and facilitating less-invasive implant techniques. The fixation device is implanted first and provides a mounting fixture for the subsequently delivered permanent valve (Continued)

assembly. In some embodiments, the permanent valve assembly is at least partially mechanically isolated from the fixation device after the permanent valve assembly is attached to the fixation device. In some embodiments, the fixation device includes a temporary valve assembly that prevents regurgitation until the permanent valve assembly is implanted.

25 Claims, 13 Drawing Sheets

Related U.S. Application Data filed on Oct. 9, 2018, provisional application No. 62/742,312, filed on Oct. 6, 2018.

(52) U.S. Cl.
CPC . *A61F 2250/001* (2013.01); *A61F 2250/0059* (2013.01); *A61F 2250/0063* (2013.01)

(58) Field of Classification Search
CPC ...... A61F 2250/0059; A61F 2250/0063; A61F 2/2412; A61F 2/2433; A61F 2250/0039; A61F 2250/006; A61F 2/2418
See application file for complete search history.

(56) References Cited

U.S. PATENT DOCUMENTS

| | | |
|---|---|---|
| 2009/0281609 A1 | 11/2009 | Benichou et al. |
| 2014/0214154 A1 | 7/2014 | Nguyen et al. |
| 2014/0303719 A1* | 10/2014 | Cox ..................... A61F 2/2466 623/2.37 |
| 2015/0335429 A1 | 11/2015 | Morriss et al. |
| 2016/0317291 A1 | 11/2016 | Bishop et al. |
| 2016/0367360 A1* | 12/2016 | Cartledge ............. A61F 2/2436 |
| 2017/0014252 A1* | 1/2017 | Kelly ................ A61M 25/0068 |
| 2017/0281337 A1 | 10/2017 | Campbell |
| 2017/0360561 A1 | 12/2017 | Bell et al. |
| 2018/0228607 A1 | 8/2018 | Alon et al. |
| 2018/0243086 A1 | 8/2018 | Barbarino et al. |

FOREIGN PATENT DOCUMENTS

| | | |
|---|---|---|
| WO | 2012106602 A2 | 8/2012 |
| WO | 2013059743 A1 | 4/2013 |
| WO | 2016011185 A1 | 1/2016 |
| WO | 2016172349 A1 | 10/2016 |
| WO | 2017041029 A1 | 3/2018 |
| WO | 2018057257 A1 | 3/2018 |
| WO | 2020073056 A1 | 4/2020 |

OTHER PUBLICATIONS

PCT Search Report and Written Opinion, Appl. No. PCT/US19/55063, dated Dec. 13, 2019, 16 pages.
First Office Action dated Jan. 10, 2024 in Chinese Patent Application No. 201980081133.7, 18 pages.

* cited by examiner

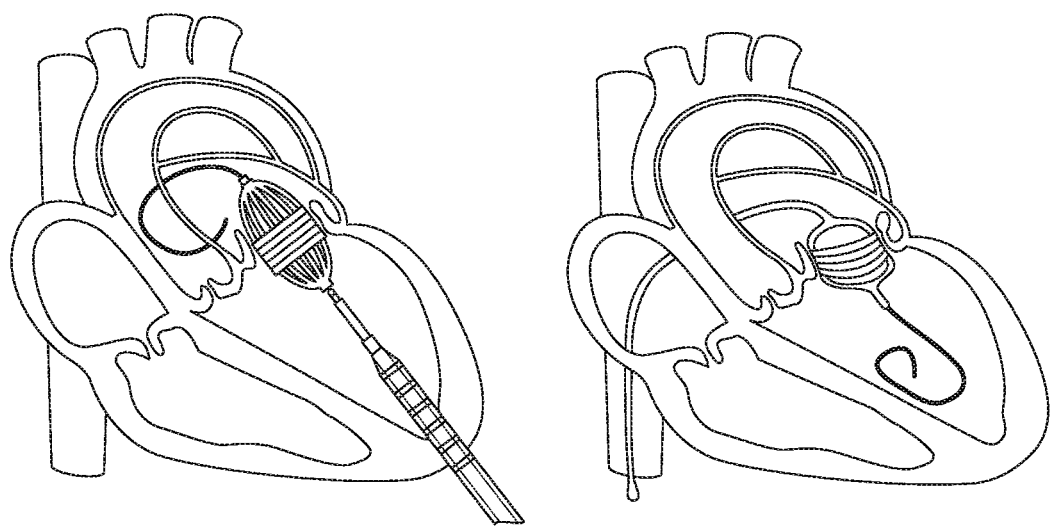
*Fig. 3A*  *Fig. 3B*
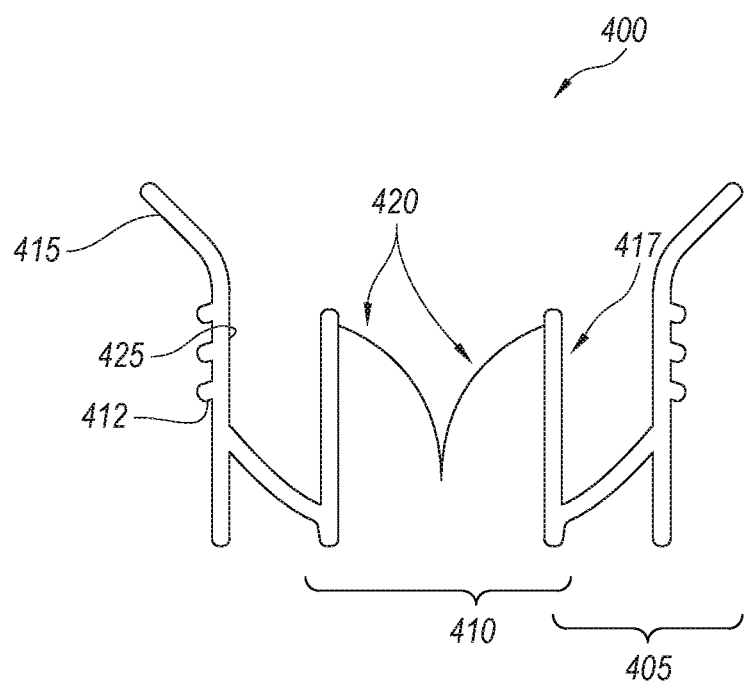
*Fig. 4*

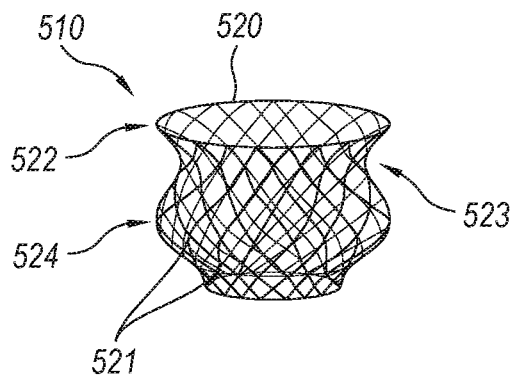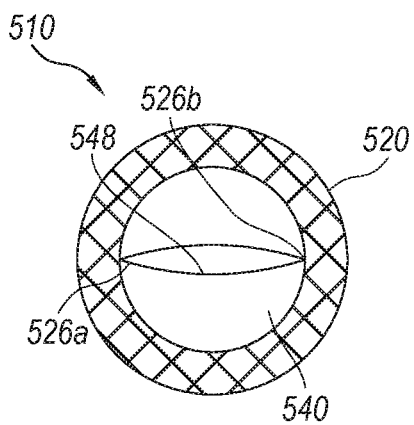
Fig. 5A    Fig. 5B
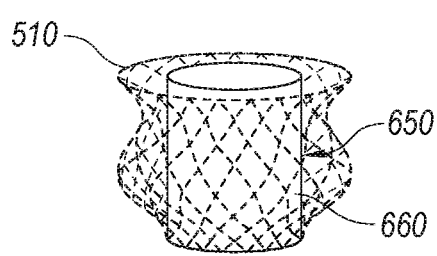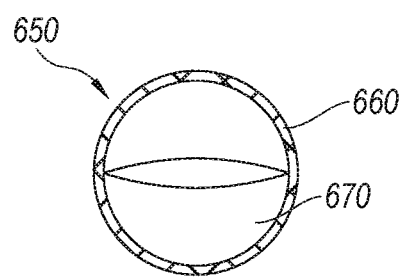
Fig. 6A    Fig. 6B

MODULAR VALVE REPLACEMENT SYSTEMS AND ASSOCIATED DEVICES AND METHODS OF USE

CROSS-REFERENCE TO RELATED APPLICATION(S)

The present application is a 35 U.S.C. § 371 U.S. National Phase application of International Application No. PCT/US2019/055063, filed Oct. 7, 2019, which claims priority to U.S. Provisional Patent Application No. 62/742,312, titled "MODULAR APPARATUS FOR ANNULAR FIXATION OF TRANSCATHETER VALVE," filed Oct. 6, 2018, U.S. Provisional Patent Application No. 62/766,193, titled "MODULAR APPARATUS FOR ANNULAR FIXATION OF TRANSCATHETER VALVE," filed Oct. 9, 2018, and U.S. Provisional Patent Application No. 62/851,595, titled "INTERVENTIONAL MODULAR FIXATION APPARATUS AND CARDIAC VALVE DEVICES, SYSTEMS, AND ASSOCIATED METHODS OF USE," filed May 22, 2019, the disclosures of which are hereby incorporated by reference in their entireties.

TECHNICAL FIELD

The present technology relates to interventional devices and associated systems and methods of use. In particular, the present technology is directed to interventional devices, systems, and methods for improving function of cardiac valves, such as treating mitral valve regurgitation.

BACKGROUND

Mitral valve regurgitation is one of the most prevalent forms of valve disease. Mitral valve regurgitation is especially impactful in an aging population in the developing world where it affects approximately 10% of those older than 75 years of age. Mitral valve regurgitation is a health issue because mitral valve incompetence causes an increased volume of blood to be pumped back or retained in the left atrium and pulmonary circulation, which places increased strain on the left ventricle. This can cause irreversible left ventricular damage and even decompensation. Mitral valve replacement or repair can be an efficacious treatment for some patients with mitral valve regurgitation, yet up to half of the patient population is not referred for mitral valve replacement or repair surgery due to a perceived risk of such procedures.

Mitral valve regurgitation is typically due to a reduction of functional competence of the mitral valve, which relies on a variety of anatomical structures and coordinated interaction of the left ventricle, papillary muscles, chordae tendineae, anterior leaflet, posterior leaflet, and the mitral valve annulus. Damage to any one of those structures can impact valve function or competence. Mitral valve regurgitation is categorized as degenerative or functional (or primary or secondary, respectively). Functional mitral valve regurgitation is typically defined as regurgitation in the setting of normal valve leaflets, which is associated with incomplete mitral valve leaflet coaptation (drawing together and/or overlap of the leaflets) often due to dilation of the annular area or left ventricular dysfunction. The depth and length of coaptation is associated with mitral valve function. Examples include ischemic mitral valve regurgitation and dilated cardiomyopathy. Degenerative mitral valve regurgitation examples include leaflet perforations, prolapse, rheumatic valve disease, or mitral annular calcification. Therefore, there is a significant need to develop efficacious devices and procedures to treat mitral valve regurgitation.

BRIEF DESCRIPTION OF THE DRAWINGS

FIGS. 3A-3B illustrate transapical and trans-septal implant techniques, respectively, for implanting a medical device into a heart.

FIG. 4 is a side view of a valve replacement assembly having a valve assembly permanently affixed to a fixation apparatus.

FIGS. 5A-5B illustrate a fixation device for a modular valve replacement system configured in accordance with select embodiments of the present technology.

FIGS. 6A-6B illustrate a modular valve replacement system with a valve assembly attached to the fixation device illustrated in FIGS. 5A-5B in accordance with select embodiments of the present technology.

DETAILED DESCRIPTION

Figures 1A, 1B:
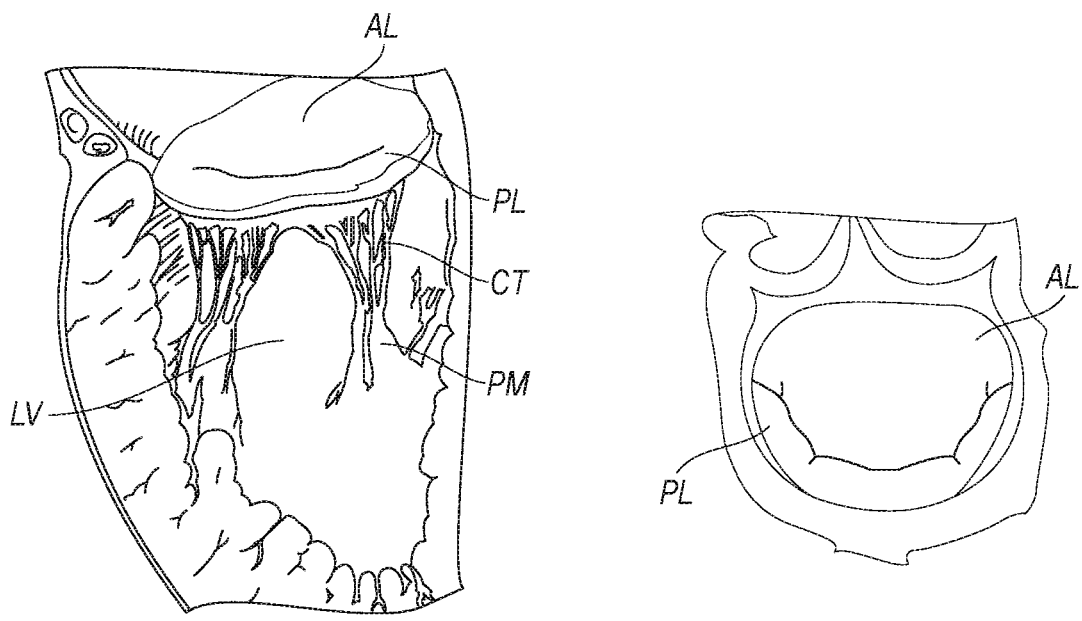
FIGS. 1A-1B are side views and top views, respectively, of mitral valve anatomy.

The present technology relates to modular valve replacement systems for treating valve-related cardiac disorders. In select embodiments, the modular valve replacement system includes a fixation device and a permanent valve assembly configured to be assembled in vivo. The fixation device and the permanent valve assembly are delivered separately, enabling use of smaller delivery systems and facilitating less-invasive implant techniques. The fixation device is implanted first and provides a mounting fixture to which the permanent valve assembly is subsequently attached. In some embodiments, the fixation device includes a temporary valve assembly that prevents regurgitation until the permanent valve assembly is implanted. After the fixation device has been implanted, the permanent valve assembly can be inserted into the heart and attached to the fixation device. The permanent valve assembly can include a frame and a permanent prosthetic valve carried by the frame, and the frame can be configured to be securely connected to the fixation device while the fixation device and the permanent valve assembly are within the heart.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1A-14.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "substantially," "approximately," and "about" are used herein to mean the stated value plus or minus 50%, 20%, 10%, 5%, 2%, 1%, or less than 1%.

As used herein, the term "fixation device" refers to an implantable medical apparatus that provides a mounting fixture for subsequent delivery and attachment of a valve assembly (e.g., a permanent valve assembly). The fixation device can optionally include a temporary valve assembly.

As used herein, the term "temporary valve assembly" refers to one or more features of a fixation device that at least partially reduce and/or mitigate regurgitation following implantation of the fixation device but before delivery of a permanent valve assembly.

As used herein, the terms "permanent valve assembly," "permanent valve device," "valve replacement assembly," "valve replacement device," and "valve assembly" refer to a structure having a prosthetic valve that is configured to be delivered to and securely attached to a previously implanted fixation device. Use of the term "permanent" does not require that the valve is indefinitely implanted. Rather, use of the term "permanent" simply distinguishes the "permanent valve assembly" from the temporary valve assembly. For example, a "permanent valve assembly" is one that is implanted and intended to remain in the patient after completing the procedure and the patient leaves the medical facility for as long as the modular valve replacement system functions adequately.

The headings provided herein are for convenience only and do not interpret the scope or meaning of the claimed present technology.

I. Mitral Valve Anatomy

Figure 2:
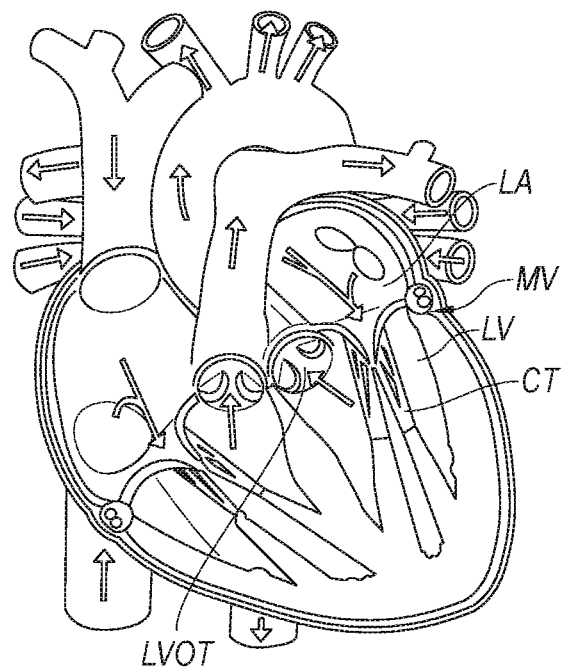
FIG. 2 is a partial schematic illustration of blood flow paths through a human heart.

The mitral valve controls the flow of blood between the left atrium and the left ventricle. In a healthy heart, the mitral valve is open during diastole and allows blood to flow from the left atrium to the left ventricle. The mitral valve closes during systole to prevent flow of blood from the left ventricle to the left atrium. As a result, the left ventricle contracts and pumps blood out via the aorta without pumping blood back into the left atrium. Failure of the mitral valve to prevent the backflow of blood from the left ventricle to the left atrium is known as mitral valve regurgitation. FIG. 1A is a side view of native mitral valve anatomy, FIG. 1B is a top view of native mitral valve anatomy, and FIG. 2 is a schematic illustration of the path of blood flow through a heart. As illustrated, the mitral valve is a bicuspid valve comprising an anterior leaflet AL and a posterior leaflet PL. A plurality of tendon-like fibrous structures called chordae tendineae CT attached to the ventricular side of the anterior and posterior leaflets prevent prolapse of the leaflets. The chordae tendineae CT are secured to papillary muscles PM projecting from the walls of the left ventricle LV. Referring to FIG. 2, blood flows from the left atrium LA to the left ventricle LV via the mitral valve MV. Blood flows out of the left ventricle LV into the ascending aorta via the left ventricular outflow tract LVOT.

II. Transcatheter Mitral Valve Repair and/or Replacement

Transcatheter technologies to repair or replace the mitral valve (often referred to as TMVr and TMVR) seek to reduce the perceived risk of mitral valve replacement/repair procedures. For example, several existing techniques seek to deliver an interventional device using a catheter-based delivery system. However, there are many challenges in implementing catheter-based interventional devices to treat mitral regurgitation because of the complexity of the mitral valve anatomy and the wide variety of both the mitral valve anatomy and the disease state across individual patients. Additionally, existing mitral valve repair devices often result in incomplete restoration of mitral valve function.

A variety of transcatheter mitral valve replacement device systems have been developed. Existing valve replacement systems typically have an implantable device comprising an attachment structure and a prosthetic valve structure permanently attached to the attachment structure. The attachment structure secures and seals the device to the native valve, and the prosthetic valve replaces the function of the native leaflets.

In TMVR, the valve replacement device is delivered in a compressed state via a delivery catheter. Transcatheter delivery techniques include transapical, trans-septal, and transfemoral. FIG. 3A illustrates a transapical delivery technique and FIG. 3B illustrates a trans-septal delivery technique. These techniques are well described in the literature and have been used for other cardiologic procedures. These procedures are typically performed using fluoroscopic, echocardiographic, and other imaging guidance. In the catheter-based delivery techniques, a steerable guidewire is placed across the orifice of the mitral valve. The delivery catheter with a compressed interventional device is inserted and located at the annular region of the native valve. The interventional device is then released from the catheter where it self-expands or is expanded (e.g., via balloon expansion) to a deployed state in which it is in apposition with the native valve anatomy. The catheter is then removed from the patient.

The dimensions of valve replacement devices, particularly as loaded or compacted for delivery, are a substantial driver for the outer diameter (often referred to as "French size") of the catheter-based delivery device. The cross-sectional or radial dimensions of the valve replacement dimensions as loaded are often referred to as the packing density. Most existing TMVR systems, for example, require a transapical approach where a catheter is inserted between the ribs to enter the apex of the heart to deliver the interventional device. This is because existing TMVR systems have unique constraints to be effective in native mitral valves, which impact the shaft size and stiffness of the as-loaded device and delivery system. Transapical approaches, however, are often considered less desirable due to the degree of myocardial injury and the impact of a thoracotomy (i.e., the surgery to access the pleural space via between the ribs), and in particular for older patients in poor health.

FIG. 4 is a cross-sectional view of a valve replacement device 400 (referred to herein as "device 400") having an attachment structure 405 and a valve structure 410 permanently attached to the attachment structure 405. FIG. 4 illustrates the device 400 in the deployed state, although the attachment structure 405 and the valve structure 410 are also permanently attached before being deployed. The attachment structure 405 is configured to secure and seal the device 400 to the native anatomy. The attachment structure 405 can include fixation member 425 (e.g., fixation ring), fixation elements 412 (e.g., barbs) projecting from the fixation member 425, and an atrial "brim" 415 extending from an upstream portion of the fixation member 425. The valve structure 410 can include a valve support 417 and a prosthetic valve 420 attached to the valve support 417. The device 400 is advantageous, for among other reasons, because the valve support 417 is mechanically isolated from the fixation member 425 so that a tri-leaflet valve can be used in the valve support 417. The fixation member 425 securely retains the device at a desired location relative to the anatomy. However, the compressed cross-sectional and longitudinal dimensions of the combined structures of the attachment structure 405 and permanently attached valve structure 410 may limit implementation of the device 400. For example, the outer diameter size of a delivery device capable of delivering device 400 may be too large for certain implant techniques. Additionally, the valve replacement device 400 is relatively stiff in the compacted state such that it is difficult to insert the device 400 through tight bends in the vasculature and to turn the device 400 within the atrium for properly positioning the device at the native mitral valve.

Accordingly, reducing the outer diameter of the delivery device would be advantageous to reduce trauma to the heart using a transapical approach, as well as reducing the size of the access opening and risk of bleeding out. Reducing the outer diameter of the delivery device would also enable other techniques for delivering the interventional device to the mitral valve, such as trans-septal or trans-atrial. Trans-septal techniques are considered advantageous because they reduce trauma to the heart and allow more peripheral access, and reducing procedure trauma is associated with improved patient outcomes and shortened recovery times.

Reducing the system stiffness of a loaded delivery device would also be beneficial to enable trans-septal or other less invasive techniques. For example, since catheter-based trans-septal techniques require the catheter make several tight bends to access the mitral valve, reducing the stiffness of the system enables the catheter to access the native mitral valve from more peripheral locations. Collectively, reducing the stiffness of the system and reducing the compressed diameter of the interventional device would reduce the outer diameter of the catheter shaft and/or increase the flexibility and bend radius of the loaded delivery system.

Additionally, the performance of existing TMVR devices is challenged by complexities of the mitral valve and surrounding anatomy. For example, the left ventricular outflow tract (LVOT) is often decreased or obstructed by existing TMVR devices or mitral surgical valves. This interferes with the flow out of the left ventricle and through the aortic valve to the aorta. Affecting the LVOT can occur if: (a) an interventional device protrudes too far into the left ventricle, (b) the interventional device is placed at such an acute angle relative to the LVOT that it causes systolic anterior motion (SAM) of the anterior mitral leaflet, and/or (c) the anatomy otherwise constricts or redirects the LVOT in such a way that it is impacted by the device (such as septal hypertrophy). Procedure pre-planning to assess the potential for LVOT obstruction is time-consuming, and the overall concern about LVOT obstruction potentially reduces the number of patients considered for TMVR utilizing current devices.

It is also challenging to anchor and seal existing replacement valve devices that are delivered via a catheter-based technique. The native mitral anatomy to which the interventional valve device is attached is a dynamic D-shaped structure with heterogenous stiffness. As such, this presents a difficult landing zone for anchoring and sealing interventional valve devices. The D-shaped asymmetry of the native mitral valve anatomy can also be problematic for creating a replacement valve that both maintains function as a directional valve and adequately seals to the surrounding asymmetrical anatomy.

Additionally, the asymmetry of the mitral valve anatomy, potential for LVOT obstruction, and potential for adjacent structure damage, such as chordae tendineae, collectively make it difficult to target the mitral valve and implant the interventional device at a desired angle and insertion depth relative to the native anatomy. These challenges can add to complexity of the TMVR valve device and the delivery system, as well as the procedure time required to place the valve.

Therefore, there remains a need for improved cardiac valve devices, especially mitral valve replacement devices and systems. The present technology is directed to interventional devices, systems, and methods. In particular, the present technology is related to improving function of cardiac valves, and more particularly treating mitral valve regurgitation. For example, select embodiments of the present technology provide TMVR devices that overcome one or more of the challenges discussed above. Some aspects of the present technology comprise a fixation device that can accept insertion or attachment of a separate permanent valve assembly. In some embodiments, the fixation device utilizes a temporary valve reinforcement or replacement. Some aspects of the present technology comprise a permanent valve assembly with features to aid in attachment or sealing to a fixation device. In modular systems of the present technology, the fixation device is delivered separately from the permanent valve assembly. For example, one catheter access can be used for delivery of the fixation device, and another catheter access can be used for delivery of the permanent valve assembly. This reduces the diameter of the device and packing density per access compared to devices in which the fixation device is attached to the prosthetic valve apparatus during delivery, which in turn reduces the catheter diameter and increases the bend radius.

III. Select Embodiments of Modular Valve Replacement Systems

FIGS. 5A-14 illustrate select aspects of modular valve replacement systems configured in accordance with the present technology. Additional features and aspects are described as well. As one skilled in the art will appreciate from the disclosure herein, features and aspects of any particular embodiment can be applied to or otherwise incorporated with any other embodiment described in FIGS. 5A-14.

FIGS. 5A-5B illustrate a fixation device 510 configured in accordance with select embodiments of the present technology. The fixation device 510 can be implanted at or adjacent a native valve annulus to provide a mounting fixture for a subsequently delivered permanent valve replacement assembly, as described in greater detail below. Referring to FIG. 5A, the fixation device 510 includes an outer structure 520 having an upstream portion 522 and a downstream portion 524. The outer structure 520 can be a stent-like structure comprising a plurality of struts 521. The outer structure 520 can be a laser cut and molded structure, a braided structure, or any other suitable structure for forming a landing pad for a subsequently delivered valve assembly. The outer structure 520 can be formed from a shape-memory material, such as a nickel-titanium alloy, stainless steel, or another suitable material that is capable of self-expanding from a compressed delivery state to a desired expanded state shaped to engage the native mitral valve. In some embodiments, the downstream portion 524 has a greater rigidity or stiffness than the upstream portion 522. For example, the downstream portion 524 can comprise a different material and/or comprise a number of stabilizing elements (not shown) to increase the rigidity of the downstream portion 524. As will be described below with respect to FIGS. 6A-6B, the increased rigidity of the downstream portion 524 provides more structural support for supporting a permanent valve replacement assembly, while a more flexible upstream portion 522 can flex to more closely adapt to the shape of the native mitral valve. In some embodiments, both the downstream portion 524 and the upstream portion 522 have a rigidity suitable to secure a permanent valve replacement assembly.

The fixation device 510 can have a generally hourglass shape such that, in a deployed configuration, the upstream portion 522 and the downstream portion 524 flare radially outward relative to a narrow waist region 523. When fixation device 510 is implanted at, for example, a native mitral valve annulus, the upstream portion 522 resides within a left atrium and the downstream portion 524 resides within a left ventricle. Accordingly, in some embodiments, the upstream portion 522 may be referred to as a "supra-annular portion" and the downstream portion 524 may be referred to as a "sub-annular portion." In some embodiments, fixation device 510 can have another shape configured to substantially conform to a shape of a native valve annulus. In some embodiments, the fixation device 510, and in particular at least one or both of the waist region 523 and the upstream portion 522, comprises a malleable material that conforms to the native valve annulus upon deployment of the fixation device 510. For example, the fixation device 510 can be self-expandable or balloon expandable to a number of different geometric configurations that permit tissue apposition at or adjacent the native valve annulus. The outer structure 520 is at least partially hollow such that fluid can flow through the fixation device 510 from the upstream portion 522 to the downstream portion 524. Accordingly, fixation device 510 is configured such that blood flows through fixation device 510 from the upstream portion 522 to the downstream portion 524 as blood flows from the left atrium to the left ventricle.

FIG. 5B is a top view of the fixation device 510. As illustrated, fixation device 510 can further include a temporary valve assembly 540. The temporary valve assembly 540 includes a temporary valve 548. In the illustrated embodiment, the temporary valve assembly 540 is a one-way valve comprising two flaps. However, as discussed in greater detail below, other valve-like elements can be included with the temporary valve assembly 540 in lieu of or in addition to the temporary valve 548. For example, the temporary valve 548 can comprise a duckbill valve, bi-leaflet valve, tri-leaflet valve, or the like, and/or can be a thin membrane. The temporary valve assembly 540 is secured to the outer structure 520 at first attachment portion 526a and second attachment portion 526b. The temporary valve 548 can help maintain valve competence and prevent perivalvular leakage until later placement of the permanent valve replacement assembly.

FIG. 6A illustrates an assembled modular valve replacement system configured in accordance with select embodiments of the present technology. The assembled modular valve replacement system comprises the fixation device 510 and a permanent valve assembly 650. The permanent valve assembly 650 can comprise a valve support 660 and a prosthetic valve 670. In some embodiments, the valve support 660 can be a stent-like frame cut from a metal tube and/or a braided structure. For example, the valve support 660 can be made from a shape-memory laser cut tube or braid, such as a nickel-titanium alloy. As will be described in greater detail below with respect to FIG. 8, the permanent valve assembly 650 can be transvascularly delivered and secured to the fixation device 510 after the fixation device 510 has been implanted at the native valve. Once secured to the fixation device 510, the permanent valve assembly 650 can displace the temporary valve assembly 540 and function as the primary flow control mechanism. The prosthetic valve 670 can be a one-way valve configured to reduce and/or mitigate regurgitation. In some embodiments, the prosthetic valve 670 can be a bi-leaflet valve, a tubular bi-valve (e.g., an extension of a synthetic or bioprosthetic conduit comprising the permanent valve assembly 650), a tri-leaflet valve, a duckbill valve, or any other suitable valve for controlling flow of blood within a heart. FIG. 6B is a bottom view of the permanent valve assembly 650 and illustrates a bi-leaflet prosthetic valve 670 positioned within the valve support 660.

Figure 7A:
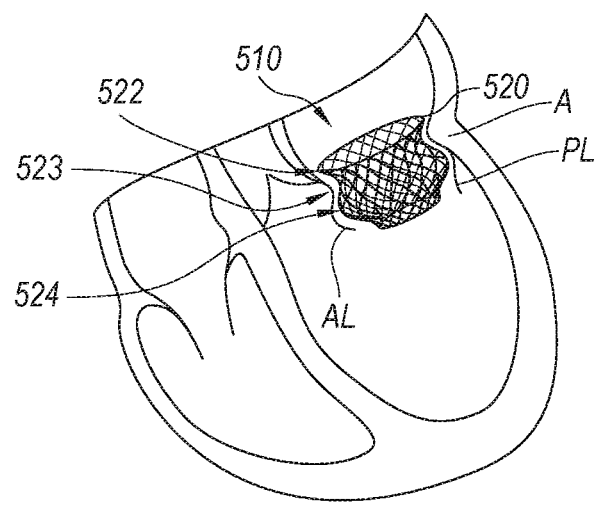
FIGS. 7A-7B illustrate implanting the fixation device of FIGS. 5A-5B at a mitral valve annulus before subsequently implanting the valve assembly of FIGS. 6A-6B in accordance with select embodiments of the present technology.

FIG. 7A is a schematic view after the fixation device 510 has been implanted at a native valve annulus A within a heart (e.g., the native mitral valve annulus). The fixation device 510 can at least partially conform to the native annulus A such that the upstream portion 522 contacts an atrial facing portion of the native annulus A, the downstream portion 524 contacts a ventricular facing portion of the native annulus A, and the waist region 523 is at inner rim of the annulus A. The anterior leaflet AL and the posterior leaflet PL are displaced by the fixation device 510. FIG. 7A illustrates the fixation device 510 before the permanent valve assembly 650 is implanted. At this stage of a procedure before the permanent valve assembly 650 is implanted, the temporary valve assembly 540 (FIG. 5B) within the fixation device 510 maintains valvular competence until the permanent valve assembly 650 is implanted and secured to the fixation device 510.

Figure 7B:
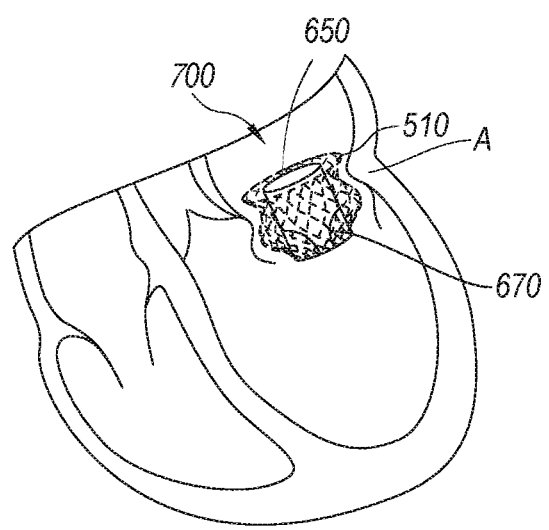

FIG. 7B illustrates the modular valve replacement system 700 after the permanent valve assembly 650 has been inserted and secured to the fixation device 510. The permanent valve assembly 650 can be secured to an interior structure of the fixation device 510 and displaces the temporary valve assembly 540 (FIG. 5B). As a result, the prosthetic valve 670 controls the flow of blood through the annulus A.

Figure 8:
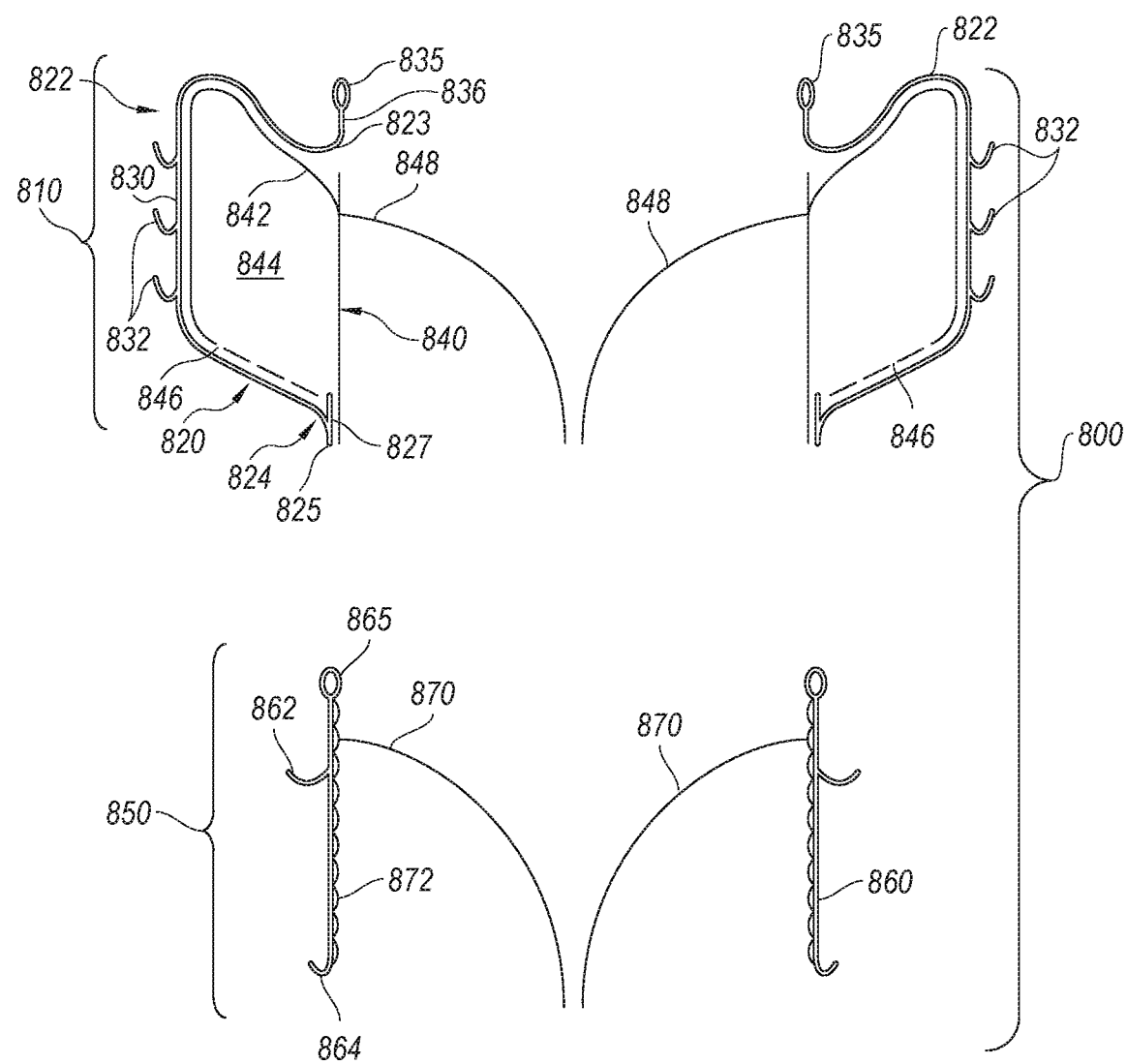
FIG. 8 illustrates a modular valve replacement system configured in accordance with select embodiments of the present technology.

FIG. 8 illustrates a modular valve replacement system 800 (hereinafter referred to as "system 800") configured in accordance with select embodiments of the present technology. The system 800 can comprise a fixation device 810 and a permanent valve assembly 850 that can be configured to be delivered separately from each other and then attached together in vivo at a target site. The fixation device 810 can have an outer structure 820 that defines a first stent structure which provides (a) fixation to the native valve anatomy, (b) support for a temporary valve to temporarily prevent regurgitant flow while just the fixation device 810 is implanted, and (c) a structure to which the permanent valve assembly 850 can be attached in vivo.

The fixation device 810 can have an outer structure 820 and a temporary valve assembly 840 attached to the outer structure 820. The outer structure 820 engages the native valve anatomy and subsequently supports the permanent valve assembly 850 within the native valve annulus. The outer structure 820 can be a self-expanding or balloon expandable first stent. For example, the outer structure 850 can be a cut tube or braid made from a shape memory material, such as a nickel-titanium alloy. In the embodiment illustrated in FIG. 8, the outer structure 820 has an upstream portion 822, a downstream portion 824, and a tissue engagement portion 830 between the upstream portion 822 and the downstream portion 824. The tissue engagement portion 830 can be a ring having a suitable shape (e.g., cylindrical or D-shaped) configured to engage and exert a radially outward force against the native annulus and/or the native leaflets. The outer structure 820 can further include fixation elements 832 projecting from the tissue engagement portion 830 that upon deployment engage the native tissue to further secure the fixation device 810 to the native anatomy.

The temporary valve assembly 840 can include an inner structure 842 configured to fit within the outer structure 820. The temporary valve assembly 840 can further include a temporary prosthetic valve 848 attached to the inner structure 842. In the embodiment illustrated in FIG. 8, the inner structure 842 forms a generally toroidal-shaped chamber 844 that can be filled with blood through apertures 846 and/or the porosity of the material from which the inner structure 842 is made. The inner structure 842 can be made from a flexible material that is attached to the outer structure 820. For example, the inner structure 842 can be made from a metal braid, polymeric materials (e.g., DACRON®), or other suitable biocompatible materials. The temporary prosthetic valve 848 can be a simple, thin structure that is configured to be displaced by the permanent valve assembly 850, as explained in more detail below.

The outer structure 820 can be symmetrical (e.g., cylindrical) as noted above such that the tissue engagement portion 830 deforms to engage the D-shaped mitral annulus. Alternatively, the outer structure 820 can be asymmetrical such that the outer structure 820 is at least partially pre-shaped to approximate the shape and contour of the mitral annulus. For example, the outer structure can a D-shape (e.g., kidney shaped). This would have the advantage of limiting the deformation of the native valve. In particular, it would limit the deformation of the anterior leaflet and aorto-mitral curtain into the left ventricular outflow tract.

The tissue engagement portion 830 is designed and shaped to engage the mitral annulus and/or the native mitral leaflets. It can be somewhat oversized relative to the annulus so that when it is deployed it engages and presses against the annulus. The tissue engagement portion 830 can be a stent with struts that define multiple diamond-shaped openings between the struts so that in the deployed state the tissue engagement portion 830 exerts an appropriate radial outward force against the native anatomy. The tissue engagement portion can alternatively be a braided portion made from nickel-titanium alloy wires with sufficient strength to apply the desired force against the annulus. The fixation elements 832 can be cleats or spikes to further engage the annulus, and in particular to resist migration of the device into the atrium under systolic ventricular blood pressure. The fixation elements 832 can extend directly outward and atrially, or they can be curved as shown in FIG. 8 so that they can be folded flat as the device is resheathed, if necessary. The tissue engagement portion 830 can also have a layer of fabric (not shown) attached to it to form a fluid seal with the annulus and to accelerate the integration of the device into the annulus wall during the healing process. The fabric can comprise a material suitable to promote tissue ingrowth.

The downstream portion 824 of the outer structure 820 extends from the tissue engagement portion 830 radially inward and distally (e.g. downstream) so that the distal end of the downstream portion 824 has a smaller inner diameter than the tissue engagement portion 830. The region of the downstream portion 824 that extends radially-inward can also have a layer of fabric (not shown) attached to it so that it will form a smooth surface to prevent clot formation over time. This fabric can be porous or have holes in it, so that blood under ventricular pressure fills the toroidal chamber 844 of the inner structure 842.

The distal end 827 of the downstream portion 824 is shaped so that the downstream-most end of the fixation device 810 forms a circular, cylindrical surface. The radially-inward-extending region of the downstream portion 824 of the outer structure 820 may have differing lengths and/or differing angles around the circumference of the stent so that it can transition from the D-shaped tissue engaging portion 830 to the circular distal end 827, as described below with respect to FIG. 14. In some embodiments, this structure can be achieved by forming the final diamond-shaped strut structure at this end of the outer structure 820 free from the adjacent proximal diamond structure and shaped such that they extend this cylindrical surface proximally.

The cylindrically shaped surface formed by the downstream portion 824 of the fixation device 810 has at least three functions. First, the downstream portion 824 retains the cylindrically-shaped inner structure 842 that defines a fabric tube which forms the chamber 844 of the temporary valve assembly 840. This tubular fabric extends in an atrial direction and then flares radially outward to join the atrial end of the tissue engagement portion 830 of the outer structure 820, as shown in FIG. 8. This fabric encloses the inner and atrial surfaces of the toroidal volume of the chamber 844. The chamber 844 is a relatively sealed chamber such that it can be inflated with blood upon deployment of the fixation device via apertures 846 and/or the porosity of fabric (e.g., on the ventricular end of the chamber 844).

Second, the cylindrical downstream portion 824 can form the attachment points for the commissures of the temporary valve 848. If it is desired to make the temporary valve assembly 840 symmetrical with a three-leaflet valve, then the outer structure 820 can comprise a number of diamond-shaped stent elements around its circumference as a multiple of three so that these commissural connections align with the stent elements. The temporary prosthetic valve 848 is sutured to the inner wall of the cylindrical fabric tube that defines the inner structure 842. The commissural suturing can project these leaflets somewhat radially towards the center of the valve so they will close predictably even after being compressed for delivery.

Third, the distal end 827 of the downstream portion 824 can be cylindrical to provide structure to which the permanent valve assembly 850 is attached after the permanent valve assembly 850 has been delivered separately from the outer structure 820. The downstream portion 824 can include specific features which engage specific features on the permanent valve assembly 850, or the permanent valve assembly 850 may simply flare outward at its distal end to engage the downstream portion 824.

The upstream portion 822 (i.e., proximal end) of the outer structure 820 extends radially inward from the upstream end of the tissue engagement portion 830. In some embodiments, it may be preferable for the upstream portion 822 to be shaped such that it extends somewhat towards the ventricle as it extends radially inward, as shown in FIG. 8. This way, when the permanent valve assembly 850 is placed inside it, any force on the valve due to systolic ventricular pressure will tend to drive the tissue engagement portion 830 outward against the native mitral annulus, rather than pulling it inward. The portion of the inner structure 842 that flares radially outward may end up laying against the upstream portion 822 of the outer structure 820.

The upstream-most and inner-most portion 836 of the upstream portion 822 bends upward (e.g., proximally), extending atrially in a generally cylindrical shape. This cylindrical surface can form a landing for the permanent valve assembly 850. This proximal end of the outer structure 820 can also have capture features 835 to releasably connect the fixation device 810 to a delivery system (not shown). The capture features 835 make it easier to recapture and recompress the fixation device 810 if necessary. In some embodiments, the upstream portion of the tissue engagement element 830, as well as the radially-inward-extending upstream portion 822, may be somewhat more flexible than the middle and distal portions of the fixation device 810, making recapture of the fixation device 810 easier. The outer structure 820 can further include first and second attachment portions 823 and 825 for securely attaching the permanent valve assembly 850 to the fixation device 810. The first attachment portion 823 is at the upstream portion 822 and the second attachment portion 825 is at the distal end 827 of the downstream portion 824. The first attachment portion 823 can include specific features which engage specific features on the permanent valve assembly 850, or the permanent valve assembly 850 may simply flare outward at its proximal end to engage the first attachment portion 823.

It some embodiments, it can be easier to compress and deliver the fixation device 810 if the total length of the proximal segments of the fixation assembly (including the upstream portion 822 that extends radially inward from the tissue engagement portion 830 and the atrially-directed upstream-most end) are all of the same length. This is the case because both the upstream portion 822 of the outer structure 820 and the connectors to the delivery system are not skewed when compressed. The lengths and angles of the proximal segments of the fixation device 810 may vary around the circumference of the fixation device 810 to achieve this, as well as to transition from a D-shaped region defined by the tissue engagement portion 830 to a circular cylindrical region defined by the upstream most end of the upstream portion 822.

FIG. 8 (bottom panel) shows a side view of the permanent valve assembly 850. In some embodiments, the permanent valve assembly 850 is a tri-leaflet valve commonly used for transcatheter valve prostheses with a diameter of about 25-30 mm. The permanent valve assembly 850 is configured to be delivered to the target site separately from the fixation device 810 and subsequently attached to the fixation device 810 in vivo. The permanent valve assembly 850 can include a valve support 860, which can be a cylindrical second stent structure that is either self-expanding or balloon-expandable. For example, the valve support 860 can be a cut tube or braided wire made from a nickel-titanium alloy or outer suitable biocompatible material. The valve support 860 can be slightly larger in diameter than the proximal and distal cylindrical segments of the outer structure 820. This will cause the valve support 860 to exert a radially outward force against the outer structure 820, which in turn will drive the outer structure 820 radially outward and further drive the tissue engagement portion 830 against the native annulus. As the heart beats, the systolic forces against the valve will push it towards the atrium. This force will be transferred to the distal and proximal radially-inward-extending portions of the outer structure 820, which will then further drive the tissue engagement portion 830 against the mitral annulus. The valve support 860 can further include first engagement elements 862 configured to engage the first attachment portion 823 of the outer structure 820, and second engagement elements 864 configured to engage the second attachment portion 825 of the outer structure 820. However, in other embodiments, the valve support is secured to the fixation device via single attachment interface.

When deployed within the fixation device 810, the permanent valve assembly 850 can remain mechanically isolated from the outer structure 820. Accordingly, deforming the outer structure 820 (e.g., to conform to native anatomy or in response to contraction of the heart) will not impart substantial force upon the permanent valve assembly 850 and therefore will not substantially affect the integrity of the valve 870.

The permanent valve assembly 850 further includes a permanent prosthetic valve 870 and a skirt 872. The skirt 872 and the permanent prosthetic valve 870 are attached to the valve support 860. The permanent prosthetic valve 870 can be a tri-leaflet valve, or any other suitable valve, such as a duckbill valve and/or a bi-leaflet valve.

In operation, the fixation device 810 is contained in a compressed state (e.g., a delivery configuration) in a delivery system. The fixation device 810 is not connected to the permanent valve assembly 850 when the fixation device 810 is in the compressed state. While the fixation device 810 is delivered to and deployed at the target location (e.g., at the native mitral valve), it is not coupled to the permanent valve assembly 850. The fixation device 810 is accordingly deployed separately from the permanent valve assembly 850. After the fixation device 810 has been implanted at the native valve annulus in a deployed or expanded state, but before the permanent valve assembly 850 is deployed, the temporary valve 848 of the temporary valve assembly 840 controls blood flow through the target valve (e.g., the mitral valve) during systole and diastole. The permanent valve assembly 850 is then deployed within the outer structure 820 such that the first and second engagement elements 862 and 864 engage the first and second attachment portions 823 and 825, respectively. As this occurs, the valve support 860 displaces the temporary valve 848 and presses radially outward against the outer structure 820. The combination of the first and second engagement elements 862 and 864 and the radially outward force between the valve support 860 and the outer structure 820 securely attaches the permanent valve assembly 850 to the outer structure 820. Additionally, since the fixation device 810 and the permanent valve assembly 850 are delivered and implanted independently of each other, they individually have a smaller compressed diameter compared to a device in which they are attached to each other before being loaded into a delivery catheter (e.g., such as the device 400 described above). This is expected to reduce the outer diameter of the delivery catheter and increase the flexibility and bend radius of the delivery system to enable peripherally-based delivery techniques, such as trans-septal or trans-atrial.

Figure 9A:
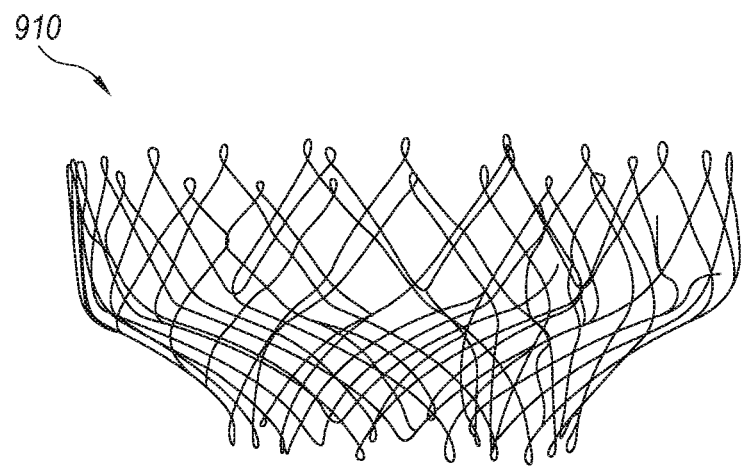
FIGS. 9A-9D illustrate aspects of a modular valve replacement system configured in accordance with select embodiments of the present technology.
Figure 9B:
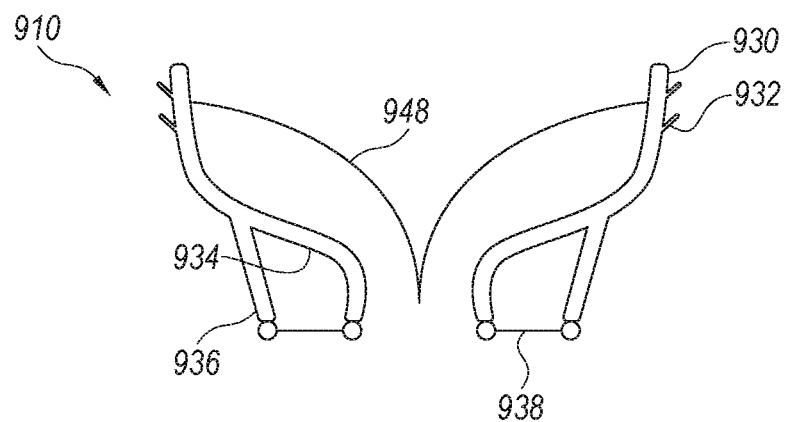

FIGS. 9A-9D illustrate additional aspects of a modular valve replacement system configured in accordance with select embodiments of the present technology. Referring to FIGS. 9A-9B, the modular valve replacement system can include a fixation device 910 configured to engage native tissue via sub-annular oversizing, radial force, and/or frictional elements (e.g., fixation elements 932). The fixation device 910 can be lined with a fabric (e.g., PET) skirt to provide sealing and a platform for ingrowth. As will be described in greater detail below, the fixation device 910 also has features that engage with the structure of a permanent valve assembly.

Referring to FIG. 9B, fixation device 910 includes a tissue engagement portion 930, valve support arms 934, and fabric support arms 936. The valve support arms 934 and the fabric support arms 936 extend from a downstream portion of the tissue engagement portion 930. In some embodiments, the valve support arms 934 and fabric support arms 936 are integral with the tissue engagement portion 930 such that together they form a unitary structure. In other embodiments, the valve support arms 934 and/or the fabric support arms 936 and the tissue engagement portion 930 are distinct elements that are otherwise coupled together. The tissue engagement portion 930 can include one or more fixation elements 932 to help secure the fixation device 910 at or adjacent the native annulus.

The valve support arms 934 extend radially inward from the downstream portion of the tissue engagement portion 930 in a similar fashion as described above with respect to the downstream portion 824 of the outer structure 820 illustrated in FIG. 8. The valve support arms 934 can be generally curved such that they form a substantially cylindrical center lumen configured to receive a permanent valve assembly. For example, in some embodiments, the valve support arms 934 define a substantially cylindrical center lumen with an inner diameter of about 20-30 mm. To form the substantially cylindrical center lumen, individual valve support arms may have varying lengths and/or curvatures to account for a non-circular outer shape of the fixation device 910.

The fabric support arms 936 extend generally downstream from the tissue engagement portion 930. As noted above, the fabric support arms 936 can simply be a downstream extension of the tissue engagement portion 930. In some embodiments, the fabric support arms 936 can be at least slightly curved and/or deformable such that they conform to native tissue. In some embodiments, the fabric support arms 936 extend radially inward at least partially such that they do not contact native tissue. In such embodiments, the fabric support arms 936 extend radially inward at a less acute angle than the valve support arms 934.

A fabric web 938 can extend between the downstream end portions of the valve support arms 934 and the downstream end portions of the fabric support arms 936. The fabric web 938 acts in tension under a ventricular pressure load to provide stability to the valve support arms 934. The valve support arms 934 and the fabric support arms 936 can also be lined with fabric to create an enclosed toroidal volume that can fill with blood 939 after implanting the fixation device 910 (see FIG. 9D). These blood-filled volumes could eventually form solid thrombus or other healing response that can provide additional stabilization of the fixation device 910. Moreover, the added stability provided to the valve support arms by the fabric web and the enclosed blood volume could allow for thinner structural elements. This can additionally reduce the pack down density without compromising structural integrity.

The fixation device 910 can have a temporary valve 948. In some embodiments, the temporary valve 948 can be generally similar to the temporary valve 848 described with respect to FIG. 8. For example, the temporary valve 948 can be made from a thin polymer material, such as ePTFE, that prevents full or partial backflow or regurgitation from the left ventricle to the left atrium, thereby reducing harmful buildup of pressure in the pulmonary system or damage to the heart.

Figure 9C:
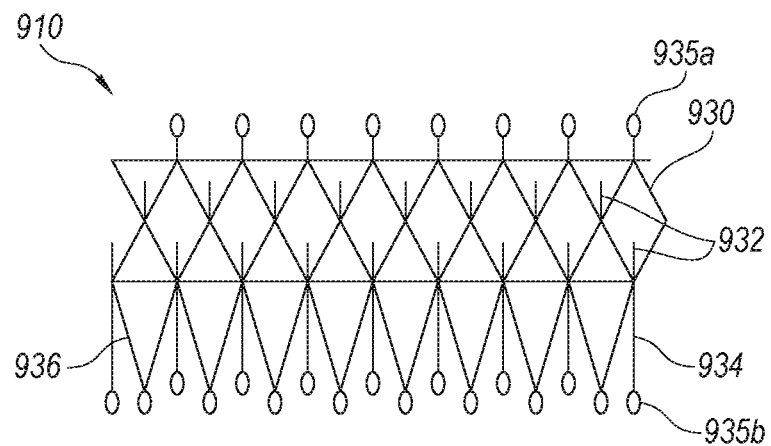

FIG. 9C depicts a flat pattern of the fixation device 910. In some embodiments, this structure is cut from a Nitinol tube and is expandable to the shape shown in FIGS. 9A-9B. The atrial end of the structure forming the tissue engagement portion 930 has a diamond pattern and fixation elements 932 that engage with the native annulus and provide fixation. A plurality of upstream capture features 935a extend atrially from the tissue engagement portion 930. The upstream capture features 935a can releasably connect the fixation device 910 to a delivery system (not shown). The upstream capture features 935a therefore make it easier to recapture and recompress the fixation device 910, if necessary. The midsection of the structure includes the valve support arms 934 and fabric support arms 936. The distal ends of the valve support arms 934 and the fabric support arms 936 are connected via the fabric web (not shown). The ventricle end of the structure can include a plurality of downstream capture features 935b to further facilitate recapture of the fixation device 910, if necessary.

As illustrated in FIGS. 9A-9C, the fixation device 910 does not include a permanent valve assembly. The modular approach therefore allows for delivery of the fixation apparatus separately from the permanent replacement valve, thus reducing the material that is packed within a given delivery catheter. This reduces maximum packing density and reduces the required catheter size.

Figure 9D:
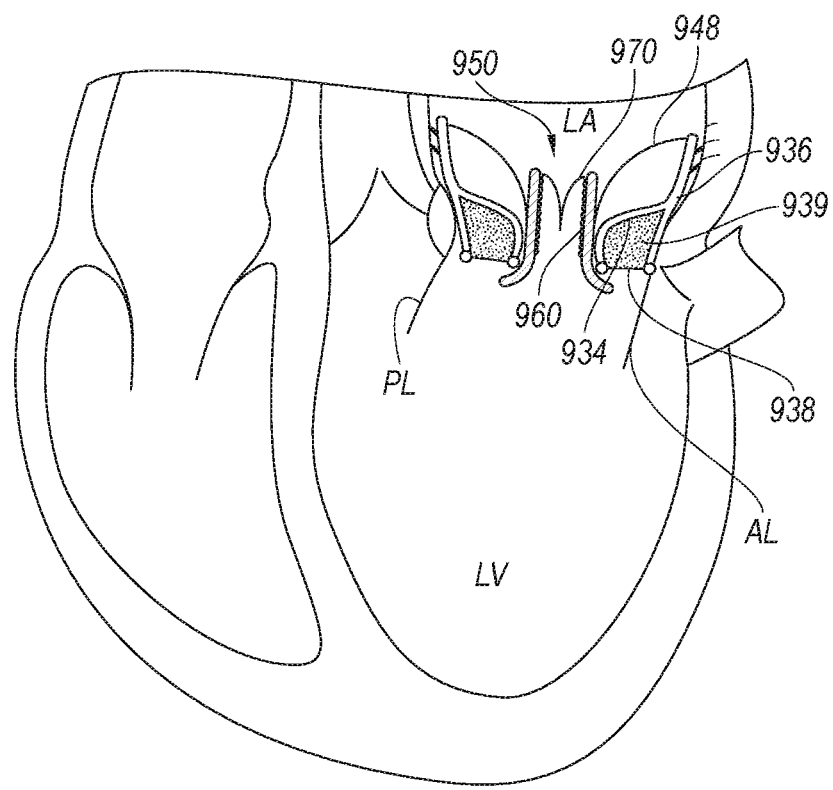

FIG. 9D depicts the fixation device 910 implanted in a heart and with a permanent valve assembly 950 engaged within the valve support arms 934. The permanent valve assembly 950 includes a valve support 960 and a prosthetic valve 970. The valve support 960 is secured to the fixation device 910 via the valve support arms 934 (e.g., through oversizing, radial force, and/or friction). The valve support 960 also supports the prosthetic valve 970, which controls the flow of blood between the left atrium and the left ventricle to reduce and/or mitigate regurgitation. As the permanent valve assembly 950 is attached to the fixation device 910, the valve support 960 displaces the temporary valve 948. In some embodiments, the permanent valve assembly 950 may be delivered from the atrial side through the same guide used to advance the delivery system of the fixation apparatus.

Figure 10A:
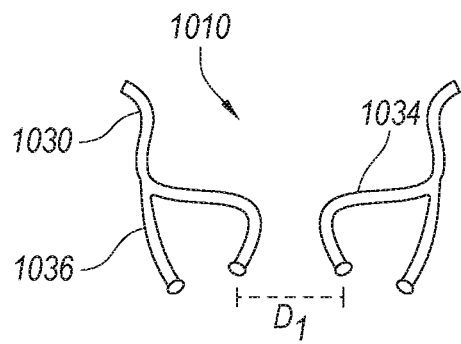
FIGS. 10A-10B illustrate aspects of another modular valve replacement system configured in accordance with select embodiments of the present technology.
Figure 10B:
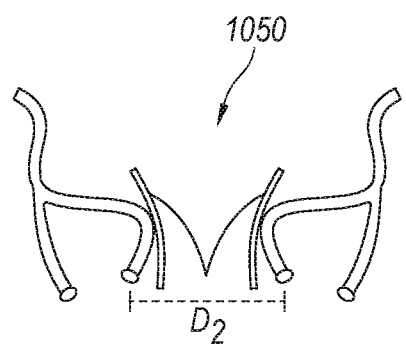

FIGS. 10A-10B are side views of a modular valve replacement system related to the embodiment described with respect to FIGS. 9A-9D. The modular valve replacement system includes a fixation device 1010 having valve support arms 1034 and fabric support arms 1036. The valve support arms 1034 can be radially over or undersized to define a central lumen having a diameter of $D_1$ (e.g., about 20-30 mm or less). The lumen can be undersized in relation to the permanent valve assembly 1050 such that insertion of the permanent valve assembly 1050 creates regioselective radial force on the valve support arms 1034, transitioning the fixation device 1010 to a second diameter $D_2$ greater than the first diameter $D_1$. Such regioselective radial forces can (a) enhance the fixation or sealing between the permanent valve assembly 1050 and the fixation device 1010, and/or (b) be transferred through the fixation device 1010 to regioselectively enhance attachment or sealing force between the fixation device 1010 and the native tissue.

Figure 11A:
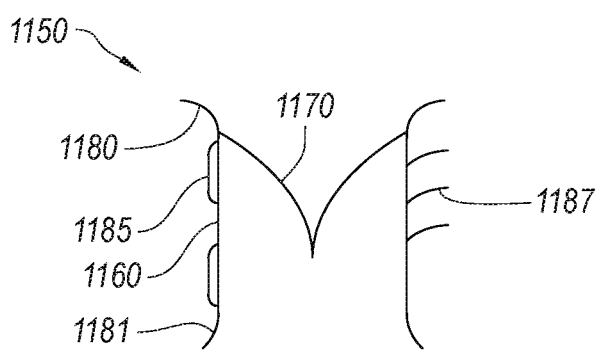
FIGS. 11A-11D illustrate valve assemblies for use with a modular valve replacement system and configured in accordance with select embodiments of the present technology.

FIGS. 11A-11D depict aspects of permanent valve assemblies that could enhance the attachment or sealing of the permanent valve assembly to the fixation assembly in any of the embodiments described herein. FIG. 11A shows a simplified side view of a permanent valve assembly 1150 including a valve support 1160 and a prosthetic valve 1170. The valve support 1160 can include a number of features that secure the permanent valve assembly 1150 to a previously implanted fixation device (e.g., fixation devices 510, 810, 910 and/or 1010). For example, the valve support 1160 can include a proximal end portion 1180 and distal end portion 1181 that curve radially outward to engage with complimentary curved structures on the fixation device to prevent longitudinal movement of the valve and potentially enhance sealing between the permanent valve assembly 1150 and the fixation device. As another example, the valve support 1160 can include hydrogel or elastomer rings or components 1185 that enhance sealing or attachment to the fixation device. As yet another example, the valve support 1160 can include barbed or other rigid or semi-rigid fixation elements 1187 to enhance attachment to the fixation apparatus. The permanent valve assemblies described herein can have one or more of the above features to help secure the permanent valve assembly to the fixation device.

Figure 11B:
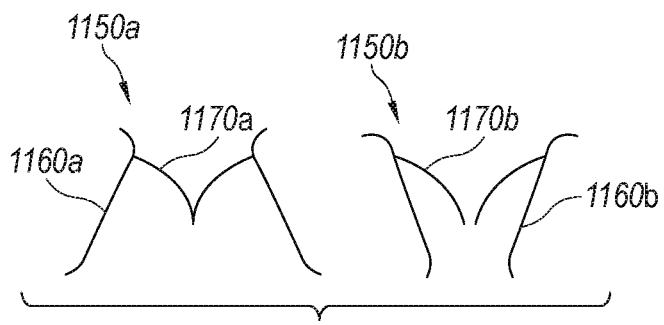
Figure 11C:
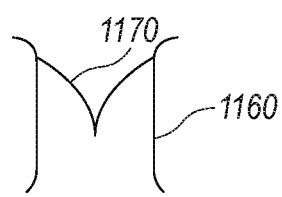

The permanent valve assemblies described herein can also be secured to the fixation devices via regioselective forces. FIG. 11B shows a side view of permanent valve assemblies 1150a and 1150b (collectively referred to as "valve assemblies 1150a b") that can be secured to the fixation devices using regioselective forces. The valve assemblies 1150a-b include respective valve supports 1160a-b and respective prosthetic valves 1170a-b. In FIG. 11B, the valve assemblies 1150a-b are depicted in a fully unconstrained state in which valve supports 1160a-b have a conical shape. FIG. 11C depicts the permanent valve assemblies 1150a-b in a constrained state that they would have when deployed within the fixation device. In lieu of or in addition to the shape of the valve support 1260a-b, regioselective force could similarly be imparted by utilizing stiffer nitinol structures or doubling up stent structures in certain regions.

Figure 11D:
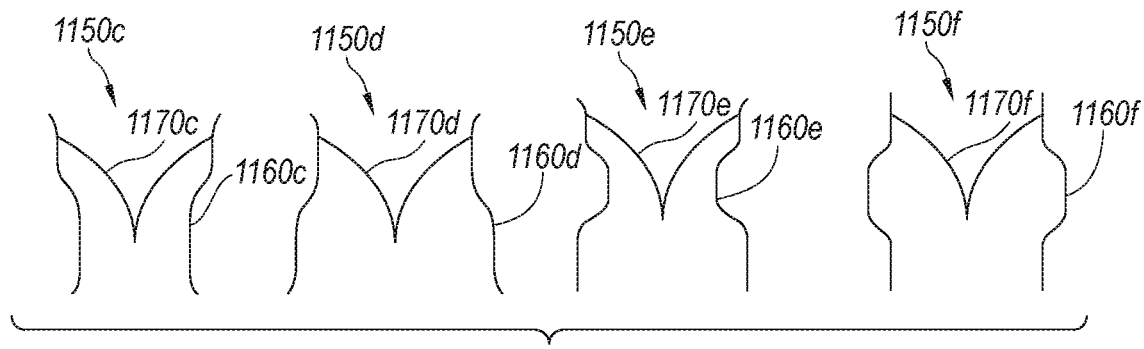

FIG. 11D shows side views of additional permanent valve assemblies configured to provide regioselective forces on the fixation device when deployed within the fixation device. For example, permanent valve assemblies 1150c-f can have valve supports 1160c-f with various non-linear shapes in a fully unconstrained state. When deployed within a fixation device in a constrained state, the valve supports 1160c-f may be prevented from fulling expanding to their unconstrained state, thereby imparting regioselective forces on and securing the valve supports to the fixation device. In some embodiments, the fixation apparatus can have complimentary profiles to improve sealing and attachment of the valve supports, and potentially targeting and depth assessment of the permanent valve relative to the fixation apparatus.

Additional techniques can also be utilized to further secure the permanent valve assembly to the fixation device. For example, once the permanent valve assembly is deployed within the fixation device, a biocompatible polymer or hydrogel (e.g., PEG) can be injected into the volume between the permanent valve assembly and the fixation apparatus to seal the permanent valve to the fixation device and promote attachment.

Figure 12A:
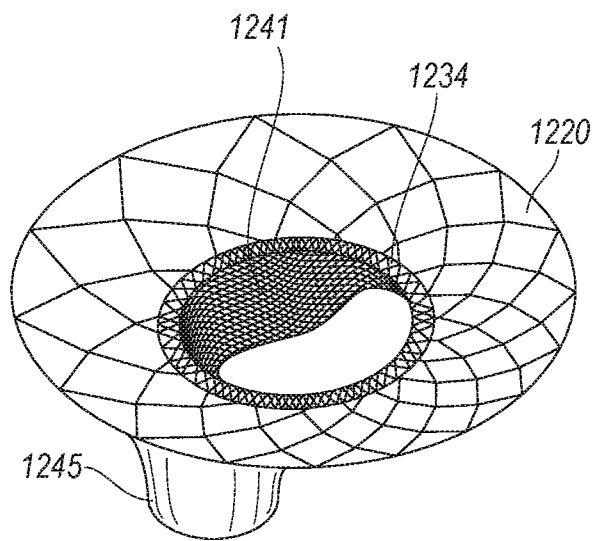
FIGS. 12A-12E illustrate aspects of a modular valve replacement system configured in accordance with select embodiments of the present technology.
Figure 12B:
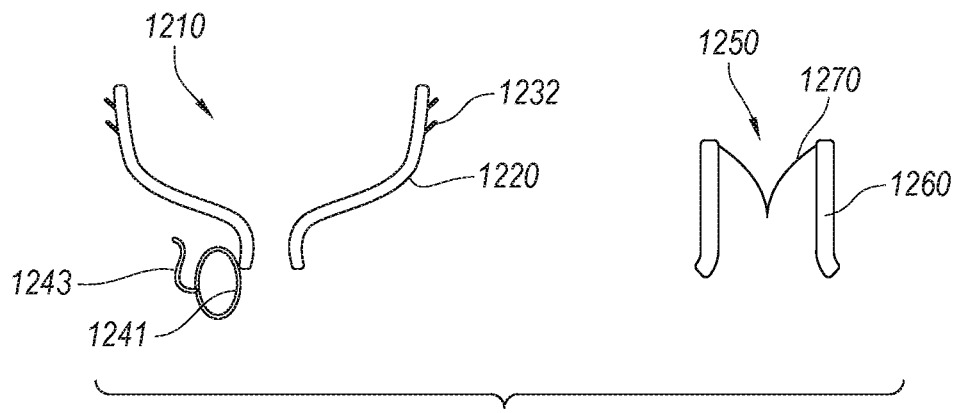
Figure 12C:
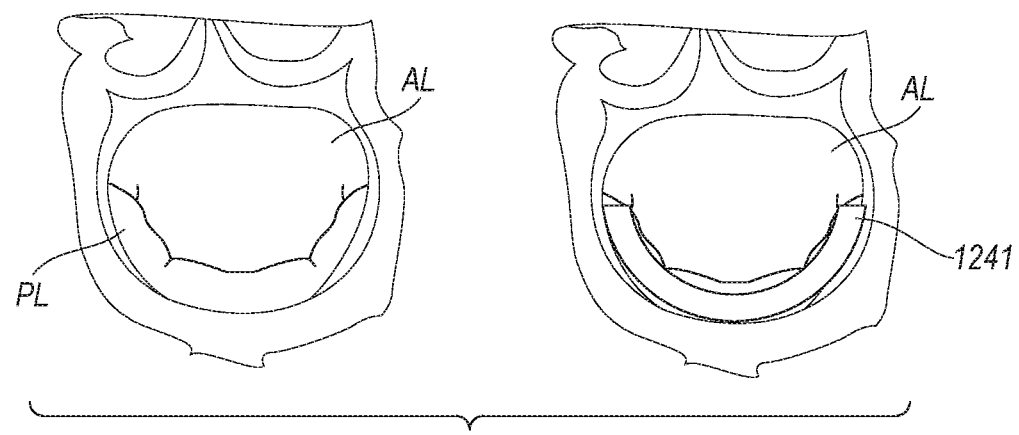

FIGS. 12A-12E illustrate yet another fixation device 1210 configured in accordance with select embodiments of the present technology. Referring to FIGS. 12A and 12B, the fixation device 1210 includes an outer structure 1220 and a temporary flow restriction element 1234. Rather than having a bi-leaflet valve, the temporary flow restriction element 1234 includes a single moveable element or flap, such as prosthetic leaflet 1241. The prosthetic leaflet 1241 is coupled to a distal (e.g., ventricular) surface 1245 of the fixation device 1210 and may be moveable or fixed, but is shaped and positioned such that it coapts with a native anterior leaflet when implanted. FIG. 12C illustrates the area of the mitral valve (e.g., the posterior leaflet) that would be supplanted by the prosthetic leaflet 1241. Returning to FIG. 12B, the prosthetic leaflet 1241 can include a clip 1243. The clip 1243 can engage the native leaflet (e.g., the posterior leaflet) blocked by the prosthetic ventricular surface 1245. Engaging the native leaflet with the clip 1243 may help to prevent systolic anterior motion of the native leaflet, and may reduce impingement of the native leaflet and or fixation device 1210 into the LVOT. The fixation device 1210 can also include valve support arms in which the permanent replacement valve can be engaged (not shown). This system minimizes LVOT obstruction and does not require a temporary valve on the fixation apparatus, another way to potentially additionally reduce packing density.

Figure 12D:
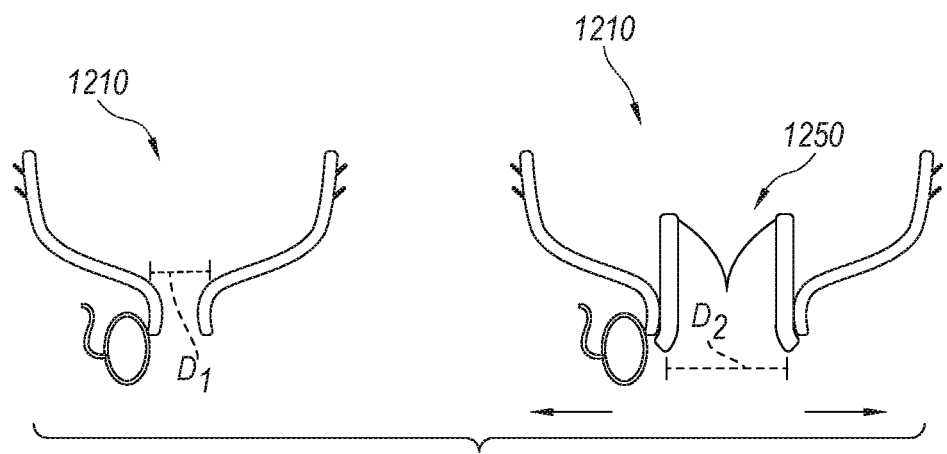
Figure 12E:
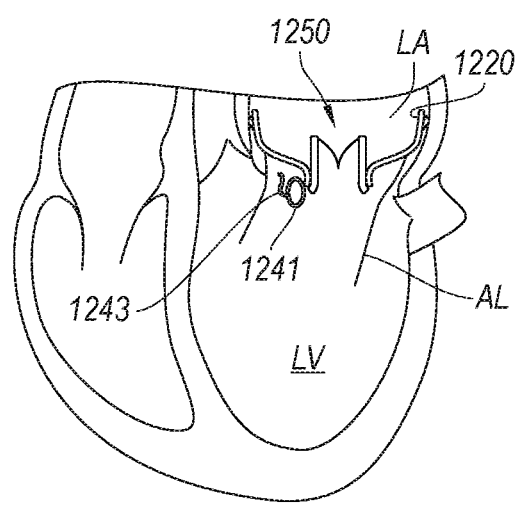

The modular valve replacement system further includes a permanent valve assembly 1250 that is attached to the fixation device 1210 after the fixation device 1210 has been implanted in the heart. The permanent valve assembly 1250 can include valve support 1260 and prosthetic valve 1270. The permanent valve assembly 1250 can be substantially similar to the permanent valve assemblies described herein. Referring to FIG. 12D, permanent valve assembly 1250 can be secured to the fixation device 1210 via regioselective forces. For example, the fixation device 1210 can have a narrowed orifice with a first diameter $D_1$ when the valve assembly 1250 is separate from the fixation device 1210. This could potentially reduce the interference with coaptation of the native anterior leaflet until the permanent valve assembly 1250 is deployed and exert more radial outward force against the fixation device 1210. This enhances the fixation and sealing both between the permanent valve assembly 1250 and the fixation device 1210, and the fixation device 1210 and the surrounding native mitral valve area. As illustrated in FIG. 12D, the fixation device 1210 engages the atrial wall via radial force and frictional elements. FIG. 12E illustrates the fixation device 1210 and the permanent valve assembly 1250 implanted in the heart.

Figure 13A:
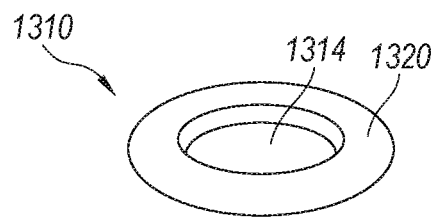
FIGS. 13A-13C illustrate a modular valve replacement system configured to reside above a native valve annulus and in accordance with select embodiments of the present technology.
Figures 13B, 13C:
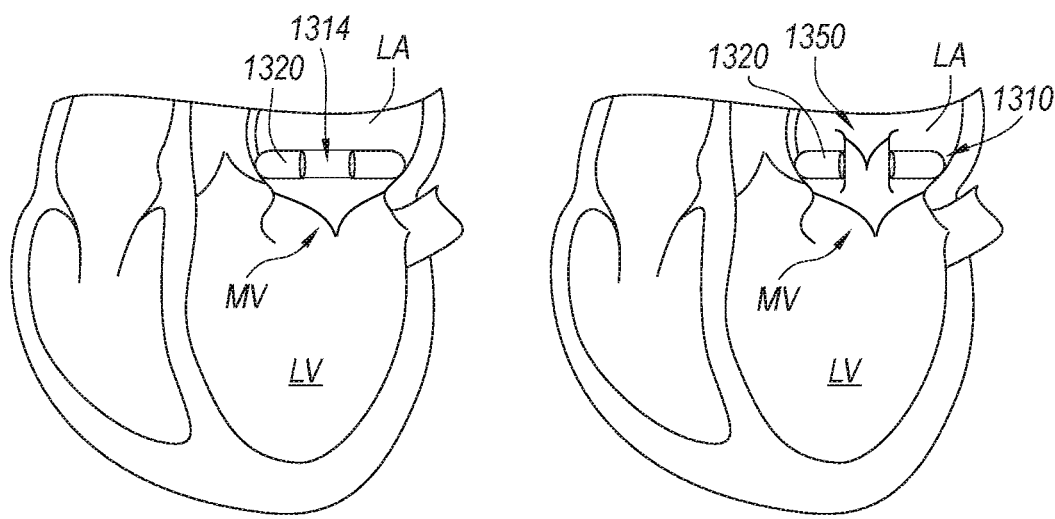

FIGS. 13A-13C illustrate a modular valve replacement system deployable above a native valve annulus (e.g., within a left atrium above a mitral valve annulus) in accordance with select embodiments of the present technology. FIG. 13A illustrates a fixation device 1310 having a lumen 1314. Although illustrated as a simple toroidal sphere, the fixation device 1310 can comprise any configuration substantially similar to configurations described herein for other fixation devices, and it can include additional elements as discussed herein. Referring to FIG. 13B, the fixation device 1310 is deployed above the native valve annulus and secured within the left atrium. As a result, the fixation device 1310 does not contact the native leaflets, and thus a temporary valve assembly is not needed to control blood flow following implantation of the fixation device 1310 but before delivery of the permanent valve assembly.

Referring to FIG. 13C, a permanent valve assembly 1350 can be subsequently delivered to and deployed within the fixation device 1310. The permanent valve assembly 1350 also sits within the left atrium and therefore does not interfere with the native leaflets. Accordingly, the permanent valve assembly 1350 supplements the functioning of the native leaflets. While FIGS. 13A-C illustrate a specific modular valve replacement system, one skilled in the art will understand that any of the modular valve replacement systems described herein, including the various features and designs of the fixation devices and permanent valve assemblies, can be configured to avoid interfering with the native valve leaflets by being deployed and secured above the native leaflets (e.g., the left atrium above the mitral valve). This embodiment would not require temporary valve leaflets, another way to reduce packing density.

Figure 14:
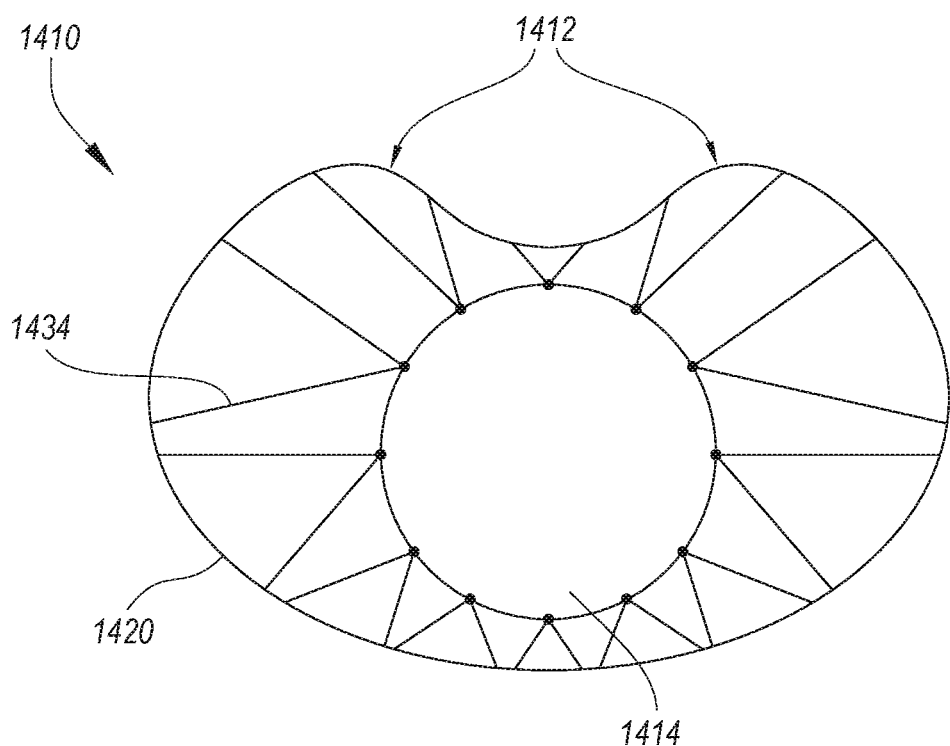
FIG. 14 is a top view of a fixation device configured in accordance with select embodiments of the present technology.

FIG. 14 is a top view of a fixation device 1410 configured in accordance with select embodiments of the present technology. The fixation device 1410 can include an outer structure 1420 and a plurality of valve support arms 1434. The plurality of valve support arms 1434 can define a generally cylindrical central lumen 1414 to which a separately delivered permanent valve assembly (not shown in FIG. 14) can be subsequently attached. The outer structure 1420 can have a kidney bean-like shape. As a result, the outer structure 1420 has two protrusions or horns 1412 that protrude to engage with native asymmetric anatomy. For example, the horns 1412 can be oriented towards the anterior side of the native valve to engage the annulus at the trigones. This is expected to enhance fixation of the fixation device 1410 to the native anatomy. The relief between the horns 1412 at the center of the anterior side of the annulus may also reduce the protrusion of the structure into the left ventricular outflow tract (LVOT) and thereby reduce the potential for LVOT obstruction. These asymmetrical shapes can be in any plane of the device and provide benefit for fixation, and in any portion of the device in the left ventricle and provide benefit in reducing LVOT obstruction. Due to the asymmetrical shape of the outer structure 1420, individual valve support arms of the plurality of valve support arms 1434 can comprise different lengths and/or shapes. This enables the outer shape to be asymmetrical while the central lumen 1414 remains substantially cylindrical. After the fixation device 1410 has been implanted, any of the permanent prosthetic valves described above can be attached to the fixation device 1410 in vivo.

The modular nature of the present technology facilitates transvascular implant approaches. For example, by separating the fixation device from the permanent valve assembly before implantation, the compressed size of the fixation device can be smaller than the combination of compressing both the fixation device and the permanent valve assembly together. For example, in some embodiments, the fixation device can be compressed to approximately 18 Fr to approximately 27 Fr, or approximately 20 Fr to proximally 25 Fr, or approximately 20 Fr to approximately 23 Fr. This enables the implantation of the fixation device in a low-profile configuration having a size less than about 27 Fr, 26 Fr, 25 Fr, 24 Fr, 23 Fr, 22 Fr, 21 Fr, 20 Fr, 19 Fr, and/or 18Fr, which in turn enhances the ability to plant the fixation device using, for example, a trans-septal approach. The permanent valve assembly can be compressed to any of the foregoing sizes of the fixation device, although the permanent valve assembly is also often compressed to smaller sizes than those listed above for the fixation device. The fixation device can accordingly be implanted first and independently of the permanent valve assembly such that the fixation device can be readily implanted at the mitral valve annulus using a trans-septal approach. The permanent valve assembly can then be positioned at the fixation device and secured thereto in vivo.

EXAMPLES

Certain aspects of the present technology, as well as various applications of the present technology, may be better understood with reference to the following examples. The following examples describe specific embodiments of the present technology but in no way limit the scope of the present technology.

1. A modular valve replacement system implantable into a heart using a catheter-based implantation system, the modular valve replacement system comprising:
   a fixation device including an outer structure having a tissue engagement portion, an upstream portion, and a downstream portion, wherein the tissue engagement portion is configured to engage native heart tissue when the fixation device is deployed within the heart to independently secure the fixation device to the native heart tissue; and
   a permanent valve assembly having a valve support and a prosthetic valve attached to the valve support, wherein the permanent valve assembly is separate from the fixation device in a low-profile state for delivery via a catheter and configured to be connected to the fixation device in vivo after the fixation device has been deployed within the heart, and the valve support is spaced inwardly apart from the tissue engagement portion when the permanent valve assembly is attached to the fixation device in vivo.

2. The modular valve replacement system of example 1 wherein:
   the downstream portion of the fixation device includes one or more valve support arms that extend radially inward from the tissue engagement portion in a deployed state and define a downstream mounting fixture; and
   the permanent valve assembly comprises an upstream end portion and a downstream end portion, and the downstream end portion of the permanent valve assembly can be connected to the downstream mounting fixture in vivo.

3. The modular valve replacement system of example 2 wherein the one or more valve support arms include distal end portions radially inward from the tissue engagement portion, and the distal end portions define the downstream mounting fixture that the permanent valve assembly can be connected to.

4. The modular valve replacement system of example 2 or 3 wherein:
   the upstream portion of the fixation device extends radially inward from the tissue engagement portion in the deployed state and defines an upstream mounting fixture configured to be connected to the upstream end portion of the valve support in vivo after the fixation device has been implanted; and
   the upstream mounting fixture and the downstream mounting fixture are substantially cylindrical.

5. The modular valve replacement system of any of examples 1-4 wherein the permanent valve assembly is configured to exert a radially outward force against the fixation device to connect the permanent valve assembly to the fixation device.

6. The modular valve replacement system of any of examples 1-5 wherein the fixation device is configured to exert a radially outward force against a native annulus of a native heart valve when deployed within the heart.

7. The modular valve replacement system of any of examples 1-6 wherein, when deployed, the tissue engagement portion has a generally curved outer surface configured to at least partially conform to the native valve annulus.

8. The modular valve replacement system of any of examples 1-7 wherein, when deployed, the tissue engagement portion is substantially D-shaped.

9. The modular valve replacement system of any of examples 1-8 wherein the tissue engagement portion comprises one or more fixation elements configured to secure the fixation device to the native heart tissue.

10. The modular valve replacement system of any of examples 1-9 wherein the fixation device further includes an inner structure having a temporary valve assembly configured to control blood flow through the fixation device before the permanent valve assembly is connected to the fixation device.

11. The modular valve replacement system of example 10 wherein the temporary valve assembly includes a temporary prosthetic valve having one or more leaflets.

12. The modular valve replacement system of example 10 or 11 wherein the permanent valve assembly is configured to displace the temporary valve assembly when the permanent valve assembly is connected to the fixation device.

13. The modular valve replacement system of any of examples 1-12 wherein, in a delivery configuration, each of the fixation device and the permanent valve assembly has an outer diameter of about 27 French or less.

14. The modular valve replacement system of any of examples 1-13 wherein the temporary valve assembly further includes an inner structure, and wherein the inner structure is generally toroidal shaped in the deployed configuration and includes—
   a radially outward facing surface configured to face an interior surface of the outer structure of the fixation device;
   a radially inward facing surface, wherein the temporary prosthetic valve projects inward from the radially inward facing surface; and
   a chamber between the radially outward facing surface and the radially inward facing surface, wherein the chamber is configured to receive blood when the fixation device is implanted at or adjacent the native valve annulus.

15. The modular valve replacement system of any of examples 1-14 wherein the fixation device is configured to be implanted at or adjacent a native mitral valve annulus.

16. A modular valve replacement system implantable into a heart using a catheter-based implantation system, the modular valve replacement system comprising:
   a fixation device including an outer structure having a tissue engagement portion and a downstream portion, wherein the fixation device is transitionable from a low-profile delivery configuration to an expanded deployed configuration, and wherein, in the expanded deployed configuration—
      the downstream end portion extends radially inward from the tissue engagement portion,
      the downstream end portion includes a valve attachment portion, and
      the tissue engagement portion is configured to engage with native heart tissue to secure the fixation device at or adjacent a native valve annulus; and
   a permanent valve assembly having (a) a support element with an upstream end portion and a downstream end portion and (b) a valve element coupled to the support element, wherein the permanent valve assembly is transitionable from a low-profile delivery configuration to an expanded deployed configuration, and wherein, in the expanded deployed configuration, the downstream end portion of the support element is configured to secure the permanent valve assembly to the fixation device at the valve attachment portion,
   wherein the fixation device is configured for deployment within the native valve annulus separately from the permanent valve assembly and the permanent valve assembly is configured to be attached to the fixation device in vivo.

17. The modular valve replacement system of example 16 wherein the fixation device further includes a temporary valve assembly configured to control blood flow through the fixation device before the permanent valve assembly is deployed and secured to the fixation device.

18. The modular valve replacement system of example 17 wherein the temporary valve assembly includes temporary prosthetic valve.

19. The modular valve replacement system of example 18 wherein the temporary prosthetic valve is a single leaflet configured to coapt with one or more native leaflets.

20. The modular valve replacement system of any of examples 17-19 wherein the temporary valve assembly further includes an inner structure, and wherein the inner structure is generally toroidal shaped in the deployed configuration and includes—
   a radially outward facing surface configured to face an interior surface of the outer structure of the fixation device;
   a radially inward facing surface, wherein the temporary prosthetic valve projects inward from the radially inward facing surface; and
   a chamber between the radially outward facing surface and the radially inward facing surface, wherein the chamber is configured to receive blood when the fixation device is implanted at or adjacent the native valve annulus.

21. The modular valve replacement system of example 20 wherein the inner structure includes one or more apertures configured to permit blood to flow into the chamber.

22. The modular valve replacement system of any of examples 16-21 wherein the permanent valve assembly is configured to displace the temporary valve assembly when the permanent valve assembly is deployed and secured to the fixation device.

23. The modular valve replacement system of any of examples 16-22 wherein, in the deployed configuration, the tissue engagement portion has a generally curved outer surface configured to at least partially conform to the native valve annulus.

24. The modular valve replacement system of any of examples 16-23 wherein, in the deployed configuration, the fixation device is configured to exert a radially outward pressure against a native valve annulus to secure the fixation device to the native valve annulus.

25. The modular valve replacement system of any of examples 16-24 wherein the tissue engagement portion comprises one or more fixation elements configured to secure the fixation device to the native valve annulus.

26. The modular valve replacement system of any of examples 16-25 wherein the fixation device is configured to be positioned upstream from a native valve annulus such that, when deployed, the fixation structure does not interfere with native leaflets in the native valve annulus.

27. The modular valve replacement system of any of examples 16-26 wherein the support element includes an engagement element, and wherein the engagement element is configured to secure the valve assembly to the fixation device at the valve attachment portion.

28. The modular valve replacement system of any of examples 16-27 wherein the support element exerts a generally radially outward force against the fixation device.

29. The modular valve replacement system of example 28 wherein, in the deployed configuration, the radially outward force secures the permanent valve assembly to the fixation device.

30. The modular valve replacement system of any of examples 16-29 wherein the modular valve replacement system is configured such that, when the permanent valve assembly is secured to the fixation device, the upstream end portion of support element of the permanent valve assembly remains mechanically isolated from the outer structure of the fixation device.

31. The modular valve replacement system of any of examples 16-30 wherein, in the delivery configuration, the fixation device has an outer diameter of about 27 French or less.

32. The modular valve replacement system of any of examples 16-31 wherein, in the delivery configuration, the permanent valve assembly has an outer diameter of about 27 French or less.

33. The modular valve replacement system of any of examples 16-32 wherein the outer portion of the fixation device is configured to exert an outward force against a mitral valve annulus.

34. A fixation device deployable at a native valve annulus for supporting a separate permanent valve assembly, the fixation device comprising:
an outer structure having a tissue engagement portion and a downstream end portion, wherein, in a deployed configuration—
the tissue engagement portion is configured to engage native heart tissue to secure the fixation device at or adjacent to a native valve annulus, and
the downstream end portion extends radially inward from the tissue engagement portion and is configured to releasably secure a permanent valve assembly implantable subsequent to the outer structure; and
a temporary valve assembly coupled to the outer structure, the temporary valve assembly having a temporary prosthetic valve configured to control blood flow through the outer structure before the permanent valve assembly is secured to the outer structure, wherein the temporary valve assembly is configured to be at least partially displaced by the permanent valve assembly.

35. The fixation device of example 34 wherein the tissue engagement portion has a generally circular or D-shaped cross-sectional shape.

36. The modular valve replacement system of example 34 or 35 wherein the tissue engagement portion has a generally curved outer surface configured to at least partially conform to the native valve annulus.

37. The modular valve replacement system of any of examples 34-36 wherein, in the deployed state, the fixation device is configured to exert a radially outward pressure against a native valve annulus to secure the fixation device at or adjacent the native valve annulus.

38. The modular valve replacement system of any of examples 34-37 wherein the tissue engagement portion includes one or more fixation elements configured to secure the fixation device at or adjacent the native valve annulus.

39. The fixation device of any of examples 34-38 wherein the fixation device is configured for transcatheter delivery with a catheter having an outer diameter of about 27 French or less.

40. A fixation device deployable at a native valve annulus for supporting a separate permanent valve assembly, the fixation device comprising:
a tissue engagement portion configured to secure the fixation device at or adjacent a native valve annulus;
a plurality of valve support arms coupled to the tissue engagement portion, wherein the plurality of valve support arms are configured to engage and secure a permanent valve assembly when the fixation device is in a deployed state; and
a temporary valve element projecting inwardly relative to the tissue engagement portion and configured to control blood flow through the fixation device before the valve replacement assembly is secured to the valve support arms.

41. The fixation device of example 40, further comprising a plurality of fabric arms extending from a downstream end portion of the tissue engagement element, wherein the plurality of fabric arms include a fabric web, and wherein the plurality of fabric arms are coupled to the plurality of valve support arms via the fabric web.

42. The fixation device of example 41 wherein the fabric web is configured to stabilize the valve support arms.

43. The fixation device of examples 41 or 42 wherein the fabric web defines an enclosed toroidal volume configured to fill with blood when the fixation device is deployed.

44. The fixation device of any of examples 40-43 wherein the fixation device is configured for transcatheter delivery with a catheter having an outer diameter of about 27 French or less.

45. The fixation device of any of examples 40-44 wherein the tissue engagement portion is configured to exert an outward force against a mitral valve annulus.

46. A method for implanting a modular valve replacement system, the method comprising:
transvascularly delivering a fixation device to a first position at or adjacent a native valve annulus using a first catheter, wherein the fixation device includes a tissue engagement element and a temporary valve assembly;
deploying the fixation device at or adjacent the native valve annulus;
after deploying the fixation device, transvascularly positioning a permanent valve assembly device within the fixation device; and
deploying the permanent valve assembly within the fixation device and thereby attaching the permanent valve assembly to the fixation device in vivo.

47. The method of example 46 wherein deploying the permanent valve assembly at least partially displaces the temporary valve assembly.

48. The method of example 46 or 47 wherein the temporary valve assembly controls blood flow through the fixation device after deploying the fixation device and before deploying the permanent valve assembly.

49. The method of any of examples 46-48 wherein the first catheter and the second catheter have outer diameters of about 27 French or less.

50. The method of any of examples 46-49 wherein the native valve annulus is a mitral valve annulus.

51. The method of any of examples 46-50 wherein transvascularly delivering the fixation device and/or transvascularly delivering the permanent valve assembly comprises delivering the fixation device and/or the permanent valve assembly using a trans-septal technique.

52. A modular valve replacement system for use with a catheter-based delivery system, comprising:
a fixation device including a tissue engagement portion and a temporary prosthetic valve having at least one prosthetic leaflet projecting inward from the tissue engagement portion, where the tissue engagement portion is configured to engage native heart tissue when the fixation device is deployed within the heart to secure the fixation device to the native heart tissue; and
a permanent valve assembly having a valve support and a prosthetic valve attached to the valve support, wherein the permanent valve assembly is separate from the fixation device in a low-profile state for delivery via a catheter and configured to be connected to the fixation device in vivo after the fixation device has been deployed within the heart, and the valve support displaces the temporary prosthetic valve when the permanent valve assembly is attached to the fixation device in vivo.

CONCLUSION

Although many of the embodiments are described above with respect to systems, devices, and methods for treating cardiac disease, the technology is applicable to other applications and/or other approaches, such as other cardiac valve applications. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-14.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Where a range of values is provided, it is understood that each intervening value, to the tenth of the unit of the lower limit unless the context clearly dictates otherwise, to between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

We claim:

1. A modular valve replacement system implantable into a heart using a catheter-based implantation system, the modular valve replacement system comprising:
a fixation device including:
an outer structure having a tissue engagement portion, an upstream portion, and a downstream portion, wherein the tissue engagement portion is configured to engage native heart tissue when the fixation device is deployed within the heart to independently secure the fixation device to the native heart tissue, and
a temporary valve assembly including a temporary prosthetic valve and an inner structure having a generally toroidal shape when the fixation device is in the deployed configuration, wherein the inner structure includes—
a radially outward facing surface configured to face an interior surface of the outer structure of the fixation device,
a radially inward facing surface, wherein the temporary prosthetic valve projects inward from the radially inward facing surface, and
a chamber positioned between the radially outward facing surface and the radially inward facing surface and configured to receive blood when the fixation device is implanted at or adjacent the native valve annulus; and
a permanent valve assembly having a valve support and a prosthetic valve attached to the valve support, wherein the permanent valve assembly is separate from the fixation device in a low-profile state for delivery via a catheter and configured to be connected to the fixation device in vivo after the fixation device has been deployed within the heart, and the valve support is spaced inwardly apart from the tissue engagement portion when the permanent valve assembly is attached to the fixation device in vivo.

2. The modular valve replacement system of claim 1 wherein:
the downstream portion of the fixation device includes one or more valve support arms that extend radially inward from the tissue engagement portion in a deployed state and define a downstream mounting fixture; and
the permanent valve assembly comprises an upstream end portion and a downstream end portion, and the downstream end portion of the permanent valve assembly can be connected to the downstream mounting fixture in vivo.

3. The modular valve replacement system of claim 2 wherein:
the upstream portion of the fixation device extends radially inward from the tissue engagement portion in the deployed state and defines an upstream mounting fixture configured to be connected to the upstream end portion of the valve support in vivo after the fixation device has been implanted; and
the upstream mounting fixture and the downstream mounting fixture are substantially cylindrical.

4. The modular valve replacement system of claim 2 wherein the one or more valve support arms include distal end portions radially inward from the tissue engagement portion, and the distal end portions define the downstream mounting fixture that the permanent valve assembly can be connected to.

5. The modular valve replacement system of claim 1 wherein the permanent valve assembly is configured to exert a radially outward force against the fixation device to connect the permanent valve assembly to the fixation device.

6. The modular valve replacement system of claim 1 wherein the temporary valve assembly is configured to control blood flow through the fixation device before the permanent valve assembly is connected to the fixation device.

7. The modular valve replacement system of claim 6 wherein the permanent valve assembly is configured to displace the temporary valve assembly when the permanent valve assembly is connected to the fixation device.

8. The modular valve replacement system of claim 1 wherein, in a delivery configuration, each of the fixation device and the permanent valve assembly has an outer diameter of about 27 French or less.

9. The modular valve replacement system of claim 1 wherein the fixation device is configured to exert a radially outward force against a native annulus of a native heart valve when deployed within the heart.

10. The modular valve replacement system of claim 1 wherein, when deployed, the tissue engagement portion has a generally curved outer surface configured to at least partially conform to the native valve annulus.

11. The modular valve replacement system of claim 1 wherein, when deployed, the tissue engagement portion is substantially D-shaped.

12. The modular valve replacement system of claim 1 wherein the tissue engagement portion comprises one or more fixation elements configured to secure the fixation device to the native heart tissue.

13. The modular valve replacement system of claim 1 wherein the fixation device is configured to be implanted at or adjacent a native mitral valve annulus.

14. A modular valve replacement system implantable into a heart using a catheter-based implantation system, the modular valve replacement system comprising:

a fixation device including:
an outer structure having a tissue engagement portion and a downstream portion, wherein the fixation device is transitionable from a low-profile delivery configuration to an expanded deployed configuration, and wherein, in the expanded deployed configuration—
the downstream end portion extends radially inward from the tissue engagement portion,
the downstream end portion includes a valve attachment portion, and
the tissue engagement portion is configured to engage with native heart tissue to secure the fixation device at or adjacent a native valve annulus; and
a temporary valve assembly including a temporary prosthetic valve and an inner structure having a generally toroidal shape when the fixation device is in the deployed configuration, wherein the inner structure includes—
a radially outward facing surface configured to face an interior surface of the outer structure of the fixation device,
a radially inward facing surface, wherein the temporary prosthetic valve projects inward from the radially inward facing surface, and
a chamber positioned between the radially outward facing surface and the radially inward facing surface and configured to receive blood when the fixation device is implanted at or adjacent the native valve annulus;
a permanent valve assembly having (a) a support element with an upstream end portion and a downstream end portion and (b) a valve element coupled to the support element, wherein the permanent valve assembly is transitionable from a low-profile delivery configuration to an expanded deployed configuration, and wherein, in the expanded deployed configuration, the downstream end portion of the support element is configured to secure the permanent valve assembly to the fixation device at the valve attachment portion,
wherein the fixation device is configured for deployment within the native valve annulus separately from the permanent valve assembly and the permanent valve assembly is configured to be attached to the fixation device in vivo.

15. The modular valve replacement system of claim 14 wherein the inner structure includes one or more apertures configured to permit blood to flow into the chamber.

16. The modular valve replacement system of claim 14 wherein the permanent valve assembly is configured to displace the temporary valve assembly when the permanent valve assembly is deployed and secured to the fixation device.

17. The modular valve replacement system of claim 14 wherein the fixation device is configured to be positioned upstream from a native valve annulus such that, when deployed, the fixation structure does not interfere with native leaflets in the native valve annulus.

18. The modular valve replacement system of claim 14 wherein the modular valve replacement system is configured such that, when the permanent valve assembly is secured to the fixation device, the upstream end portion of support element of the permanent valve assembly remains mechanically isolated from the outer structure of the fixation device.

19. The modular valve replacement system of claim 14 wherein the tissue engagement portion comprises one or more fixation elements configured to secure the fixation device to the native valve annulus.

20. The modular valve replacement system of claim 14 wherein the support element includes an engagement element, and wherein the engagement element is configured to secure the valve assembly to the fixation device at the valve attachment portion.

21. The modular valve replacement system of claim 14 wherein the support element exerts a generally radially outward force against the fixation device, and wherein in the deployed configuration, the radially outward force secures the permanent valve assembly to the fixation device.

22. The modular valve replacement system of claim 14 wherein, in the delivery configuration, the fixation device and the permanent valve assembly each have an outer diameter of about 27 French or less.

23. The modular valve replacement system of claim 14 wherein the outer portion of the fixation device is configured to exert an outward force against a mitral valve annulus.

24. A modular valve replacement system for use with a catheter-based delivery system, comprising:
   a fixation device including a tissue engagement portion and a temporary valve assembly, wherein the tissue engagement portion is configured to engage native heart tissue when the fixation device is deployed within the heart to secure the fixation device to the native heart tissue, and wherein the temporary valve assembly includes a temporary prosthetic valve having a single leaflet configured to coapt with one or more native leaflets; and
   a permanent valve assembly having a valve support and a prosthetic valve attached to the valve support, wherein the permanent valve assembly is separate from the fixation device in a low-profile state for delivery via a catheter and configured to be connected to the fixation device in vivo after the fixation device has been deployed within the heart,
   wherein the temporary valve assembly is configured to control blood flow through the fixation device before the permanent valve assembly is deployed and secured to the fixation device.

25. A modular valve replacement system for use with a catheter-based delivery system, comprising:
   a fixation device including a tissue engagement portion and a temporary prosthetic valve having (a) an inner structure having a generally toroidal shape when the fixation device is in a deployed configuration, wherein the inner structure includes a substantially enclosed chamber formed by a fabric with a plurality of apertures and/or pores configured to permit blood to flow into the chamber when the fixation device is implanted at or adjacent the native valve annulus, and (b) at least one prosthetic leaflet attached to the inner structure and projecting inward from the tissue engagement portion, where the tissue engagement portion is configured to engage native heart tissue when the fixation device is deployed within the heart to secure the fixation device to the native heart tissue; and
   a permanent valve assembly having a valve support and a prosthetic valve attached to the valve support, wherein the permanent valve assembly is separate from the fixation device in a low-profile state for delivery via a catheter and configured to be connected to the fixation device in vivo after the fixation device has been deployed within the heart, and the valve support displaces the temporary prosthetic valve when the permanent valve assembly is attached to the fixation device in vivo.

* * * * *